(12) United States Patent
Gaitan et al.

(10) Patent No.: US 9,101,939 B2
(45) Date of Patent: Aug. 11, 2015

(54) DIELECTROPHORETIC CELL CAPTURE

(71) Applicant: The National Institute of Standards and Technology, Gaithersburg, MD (US)

(72) Inventors: Michael Gaitan, North Potomac, MD (US); John T. Elliott, Silver Spring, MD (US); Jennifer Hong Gordon, Baltimore, MD (US); Darwin R. Reyes-Hernandez, Clarksburg, MD (US); Petra S. Dittrich, Zurich (CH); Conni Hanke, Zurich (CH)

(73) Assignee: THE UNITED STATES OF AMERICA, AS REPRESENTED BY THE SECRETARY OF COMMERCE, THE NATIONAL INSTITUTE OF STANDARDS AND TECHNOLOGY, Gaithersburg, MD (US)

( * ) Notice: Subject to any disclaimer, the term of this patent is extended or adjusted under 35 U.S.C. 154(b) by 214 days.

(21) Appl. No.: 13/623,925

(22) Filed: Sep. 21, 2012

(65) Prior Publication Data
US 2013/0068621 A1   Mar. 21, 2013

Related U.S. Application Data

(60) Provisional application No. 61/537,179, filed on Sep. 21, 2011.

(51) Int. Cl.
| B01D 43/00 | (2006.01) |
| G01N 27/447 | (2006.01) |
| B03C 5/00 | (2006.01) |
| B03C 5/02 | (2006.01) |

(52) U.S. Cl.
CPC ............. *B03C 5/005* (2013.01); *B03C 5/026* (2013.01); *B03C 2201/26* (2013.01); *G01N 27/447* (2013.01)

(58) Field of Classification Search
CPC ............... B03C 5/005–5/028; B03C 2201/26; C12N 11/00; C12N 11/14–11/18
USPC .......................... 204/247, 643, 547
See application file for complete search history.

(56) References Cited

U.S. PATENT DOCUMENTS

| 7,169,282 B2 | 1/2007 | Talary et al. |
| 7,425,253 B2 | 9/2008 | Voldman et al. |

(Continued)

FOREIGN PATENT DOCUMENTS

WO    WO 95/29395    * 11/1995 ............. G01N 21/00

OTHER PUBLICATIONS

Reyes et al. (Langmuir 2011, 27, 10027-10034, published Jun. 24, 2011).*

(Continued)

*Primary Examiner* — Luan Van
*Assistant Examiner* — Steven Rosenwald
(74) *Attorney, Agent, or Firm* — Mark E. Bandy; Rankin, Hill & Clark LLP

(57) ABSTRACT

Various aspects are described for selectivity capturing cells or bioparticles on designated surfaces in dielectrophoretic systems and processes. A particular adhesive composition is described for enhancing cell retention. In addition, certain permeable polyester membranes used in the systems and processes are also described.

10 Claims, 16 Drawing Sheets

(56) References Cited

U.S. PATENT DOCUMENTS

| | | |
|---|---|---|
| 2009/0071831 A1 | 3/2009 | Chen et al. |
| 2011/0123979 A1 | 5/2011 | Salmon et al. |

OTHER PUBLICATIONS

Hanke et al. (Appl. Mater. Interfaces 4, 1878-1882, published Apr. 2, 2012).*
Reyes et al. (Langmuir, 2004, 20, 8805-5511).*
Jiang (Microelectronic Engineering 88, 2011, 1722-1725).*
Gray et al. (Biosensors and Bioelectronics 19, 2004, 1765-1774).*
Reyes (14th International Conference on Miniaturized Systems for Chemistry and Life Sciences, Oct. 3-7, 2010).*
Application of dielectrophoresis in biotechnology, Ronald Pethig and Gerard H. Markx, TIBTECH, Oct. 1997 (vol. 15).
Cellular/Tissue Engineering, Joe Tien, Christopher S. Chen, IEEE Engineering in Medicine and Biology, Jan./Feb. 2002.
Dielectrophoretic separation of bacteria using a conductivity gradient, Gerard H. Markx, Penelope A. Dyda, Ronald Pethig, Journal of Biotechnology 51 (1996) 175-180.
Neutrophil chemotaxis in linear and complex gradients of interleukin-8 formed in a microfabricated device, Noo Li Jeon, Harihara Baskaran, Stephan K.W. Dertinger, George M. Whitesides, Livingston Van De Water, and Mehmet Toner, Nature Biotechnology, vol. 20, Jul. 2002.
A microfluidic chemostat for experiments with bacterial and yeast cells, Alex Groisman, Caroline Lobo, HoJung Cho, J. Kyle Campbell, Yann S. Dufour, Ann M. Stevens and Andre Levchenko, Natures Methods, vol. 2, No. 9, Sep. 2005.
Optical Trapping and Manipulation of single cells using infrared laser beams, A. Ashkin, J.M. Dziedzoc and T. Yamane, Nature vol. 330, Dec. 24/31, 1987.
Massively parallel manipulation of single cells and microparticles using optical images, Pei Yu Chiou, Aaron T. Ohta and Ming C. Wu, Nature, vol. 436, Jul. 21, 2005.
Microscopic steady streaming eddies created around short cylinders in a channel: Flow visualization and Stokes layer scaling, Barry R. Lutz, Jian Chen, and Daniel T. Schwartz, Phys. Fluids 17, 023601 (2005).
Separation of human breast cancer cells from blood by differential dielectric affinity, Frederick F. Becker, Xiao-Bo Wang, Ying Huang, Ronald Pethig, Jody Vykoukal and Peter R.C. Gascoyne, Proc. Natl. Acad. Sci. USA, vol. 92, pp. 860-864, Jan. 1995.
Emergent patterns of growth controlled by multicellular form and mechanics, Celeste M. Nelson, Ronald P. Jean, John L. Tan, Wendy F. Liu, Nathan J. Sniadecki, Alexander A. Spector and Christopher S. Chen, PNAS, 11594-11599, Aug. 16, 2005, vol. 102, No. 33.
Trapping of microparticles in the near field of an ultrasonic transducer, Tobias Lilliehorn, Urban Simu, Mikael Nilsson, Monica Almqvist, Tadeusz Stepinski, Thomas Laurell, Johan Nilsson and Stefen Johansson, Ultrasonics 43 (2005) 293-303.
Cell shape and growth of budding yeast cells in restrictive microenvironments, Masaya Suzuki, Yosuke Asada, Daisuke Watanabe and Yoshikazu Ohya, Yeast 2004, 21: 983-989.
Rapid heterogeneous liver-cell on-chip patterning via the enhanced field-induced dielectrophoresis trap, Chen-Ta Ho, Ruei-Zeng Lin, Wen-Yu Chang, Hwan-You Chang and Cheng-Hsien Liu, Lab Chip, 2006, 6, 724-734.
Optical Micromanipulation, Kishan Dholakia, Peter Reece, and Min Gu, Chem. Soc. Rev., 2008, 37, 42-55.
Optical tweezers applied to a microfluid system, Jonas Enger, Mattias Goksor, Kerstin Ramser, Petter Hagberg and Dag Hanstorp, Lab Chip, 2004, 4, 196-200.
The Science and Applications of Cell Biology in Microsystems, David Beebe and Albert Folch, Lab Chip, 2005, 5, 10-11.
Engineering Cellular microenvironments to improve cell-based drug testing, Kiran Bhadriraju and Christopher S. Chen, DDT, vol. 7, No. 11, Jun. 2002.
A novel high aspect ratio microfluidic design to provide a stable and uniform microenvironment for cell growth in a high throughput mammalian cell culture array, Paul J. Hung, Philip J. Lee, Poorya Sabounchi, Nima Aghdam, Robert Lin and Luke P. Lee, Lab Chip, 2005, 5, 44-48.
Separation of individual neurons using dielectrophoretic alternative current fields, Shalini Prasad, Xuan Zhang, Mo Yang, Yingchun Ni, Vladimir Parpura, Cengiz S. Ozkan, Mihrimah Ozkan, Journal of Neuroscience Methods 135 (2004) 79-88.
Perfusion and chemical monitoring of living cells on a microfluidic chip, Jonathan G. Shackman, Gabriella M. Dahlgren, Jennifer L. Peters and Robert T. Kennedy, Lab Chip, 2005, 5, 56-63.
Differentiation-on-a-chip: A microfluidic platform for long-term cell culture studies, Anna Tourovskaia, Xavier Figueroa-Masot and Albert Folch, Lab Chip, 2005, 5, 14-19.
Microenvironment design considerations for cellular scale studies, Glenn M. Walker, Henry C. Zeringue and David J. Beebe, Lab Chip, 2004, 4, 91-97.
Role of peroxide in AC electrical field exposure effects on Friend murine erythroleukemia cells during dielectrophoretic manipulations, Xujing Wang, Jun Yang, Peter R.C. Gascoyne, Biochimica et Biophysica Acta 1426 (1999) 53-68.
Diffusion dependent cell behavior in microenvironments, Hongmei Yu, Ivar Meyvantsson, Irina A. Shkel and David J. Beebe, Lab Chip, 2005, 5, 1089-1095.
Dielectrophoretic Cell Capture on Polyester Membranes, Conni Hanke, Petra S. Dittrich and Darwin R. Reyes, ACS Appl. Mater. Interfaces 2012, 4, 1878-1882.
Electrokinetic focusing and filtration of cells in a serpentine microchannel, Christopher Church, Junjie Zhu, Gaoyan Wang, Tzuen-Rong J. Tzeng, and Ziangchun Xuan, AIP Biomicrofluidics 3, 044109 (2009).
A planar interdigitated ring electrode array via dielectrophoresis for uniform patterning of cells, Lo-Chang Hsiung, Chun-Hui Yang, Chi-Li Chiu, Chen-Lin Chen, Yueh Wang, Hsinyu Lee, Ji-Yen Cheng, Ming-Chih Ho, Andrew M. Wo,, Biosensors and Bioelectronics 24 (2008) 869-875.
Dielectrophoretic platforms for bio-microfluidic systems, Khashayar Khoshmanesh, Saeid Nahavandi, Sara Baratchi, Arnan Mitchell, Kourosh Kalantar-zadeh, Biosensors and Bioelectronics 26 (2011) 1800-1814.
A label-free microfluidics and interdigitated array microelectrode-based impedance biosensor in combination with nanoparticles immunoseparation for detection of Esherichia coli O157:H7 in food samples, Madhukar Varshney, Yanbin Li, Balaji Srinivasan, Steve Tung, ScienceDirect, Sensors and Actuators B 128 (2007) 99-107.
General Expressions for dielectrophoretic force and electrorotational torque derived using the Maxwell stress tensor method, Xujing Wang, Xiao-Bo Wang, Peter R. C. Gascoyne, Journal of Electrostatics 39 (1997) 227-295.
Monitoring induced gene expression of single cells in a multilayer microchip, C. Hanke, S. Waide, R. Kettler, P.S. Dittrich, Anal Bioanal Chem (2012) 402: 2577-2585.
Separation-Free Sandwich Enzyme Immunoassays Using Microporous Gold Electrodes and Self-Assembled Monolayer/Immobilized Capture Antibodies, Chuanming Duan and Mark E. Meyerhoff, Anal. Chem., vol. 66, No. 9, May 1, 1994, 1369-1377.
Dielectrophoresis in Microchips Containing Arrays of Insulating Posts: Theoretical and Experimental Results, Eric B. Cummings and Anup K. Singh, Anal. Chem 2003, vol. 75, No. 18, Sep. 15, 2003, 4724-4731.
Single-Cell Enzyme Concentrations, Kinetics, and Inhibition Analysis Using HIgh-Density Hydrodynamic Cell Isolation Arrays, Dino Di Carlo, Nima Aghdam, and Luke P. Lee, Anal. Chem, vol. 78, No. 14, Jul. 15, 2006, 4925-4930.
Dynamic Analysis of Drug-Induced Cytotoxicity Using Chip-Based Dielectrophoretic Cell Immobilization Technology, Khashayar Khoshmanesh, Jin Akagi, Saeid Nhavandi, Joanna Skommer, Sara Baratchi, Jonathan M. Cooper, Kourosh Kalantar-Zadeh, David E. Williams, and Donal Wlodkowic, Anal. Chem. 2011, 83,2133-2144.
Characterization of thin gold layers on polyethyleneterephthalate: transition from discontinuous to continuous, momogenous layer, V. Svorcik, J. Zehentner, V. Rybka, P. Slepicka, V. Hnatowicz, App. Phys. A 75, 541-544 (2002).

(56) References Cited

OTHER PUBLICATIONS

DC-Dielcrophoretic separation of biological cells by size, Yuejun Kang, Dongqing Li, Spyros A. Kalams, Josianne E. Eid, Biomed Microdevices (2008) 10: 243-249.

Introducing Dielectrophoresis as a New Force Field for Field-Flow Fractionation, Ying Huang, Ziao-Bo Wang, Frederic F. Becker, and Peter R. C. Gascoyne, Biophysical Journal, vol. 73, Aug. 1997, 1118-1129.

Particle separation by dielectrophoresis, Peter R.C. Gascoyne, Jody Vykoukal, Electrophoresis 2002, 23, 1973-1983.

Trapping of DNA by dielectrophoresis, Charles L. Asbury, Alan H. Diercks, Ger van den Engh, Electrophoresis 2002, 23, 2658-2666.

Continuous separation of microparticles by size with Direct current-dielectrophoresis, Kwan Hyoung Kang, Yuejun Kang, Xiangchun Xuan, Dongqing Li, Electrophoresis 2006, 27, 694-702.

Accumulation and trapping of hepatitis A virus particles by electrohydrodynamic flow and dielectrophoresis, Frank Grom, Jorg Kentsch, Torsten Muller, Thomas Schnelle, Martin Stelzle, Electrophoresis 2006, 27, 1386-1393.

Dielectrophoretic characterization of erythrocytes: Positive ABO blood types, Soumya K. Srivastava, Prashant R. Daggolu, Shane C. Burgess, Adrienne R. Minerick, Electrophoresis 2008, 29, 5033-5046.

Dielectrophoresis in microfluidics technology, Barbaros Cetin, Dongqjuing Li, Electrophoresis 2011, 32, 2410-2427.

Simultaneous Determination of Gene Expression and Enzymatic Activity in Individual Bacterial Cells in Microdroplet Compartments, Jung-uk Shim, Luis F. Olguin, Graeme Whyte, Duncan Scott, Ann Babtie, Chris Abell, Wilhelm T. S. Huck, Florian Hollfelder, J.Am. Chem. Soc. 2009, 131, 15251-15256.

The Motion and Precipitation of Suspensoids in Divergent Electric Fields, Herbert A. Pohl, J. Appl. Phys, 22, 869 (1951).

Hybrid Cell Adhesive Material for Instant Dielectrophoretic Cell Trapping and Long-Term Cell Function Assessment, Darwin R. Reyes, Jennifer S. Hong, John T. Elliott, Michael Gaitan, Langmuir 2011, 27, 10027-10034.

Selective dielectrophoretic manipulation of surface-immobilized DNA molecules, W. Andre Germishuizen, Christoph Walti, Rene Wirtz, Michael B. Johnston, Michael Pepper, A. Giles Davies, Anton P.J. Middelberg, Nanotechnology 14, (2003) 896-902.

Marker-specific sorting or rare cells using dielectrophoresis, Xiaoyuan Hu, Paul H. Bessette, Jiangrong Qian, Carl D. Meinhart, Patrick S. Daugherty, Hyongsok T. Soh, PNAS, Nov. 1, 2005, vol. 102, No. 44, 15757-15j761.

Monolithic Microfabricated Valves and Pumps by Multilayer Soft Lithography, Marc A. Unger, et al., Science 288, 113 (2000).

Dielectrophoretic Assembly of Electrically Functional Microwires from Nanoparticle Suspensions, Kevin D. Hermanson et al., Science 294, 1082 (2001).

Microfluidics device for single cell gene expression analysis in Saccharomyces cerevisiae, James Ryley and Olivia M. Pereira-Smith, Wiley InterScience, Yeast 2006, 23: 1065-1073.

Rational Design of Cytophilic and Cytophobic Polyelectrolyte Multilayer Thin Films, Jonas D. Mendelsohn, Sung Yun Yang, Jeri Ann Hiller, Allon I. Hochbaum, Michael F. Rubner, Biomacromolecules 2003, 4, 96-106.

Microfabrication-Based Dynamic Array Cytometer, Joel Voldman, Martha L. Gray, Mehmet Toner, Martin A. Schmidt, Anal. Chem. 2002, 74, 3984-3990.

Dynamics of Drosophila embryonic patterning network perturbed in space and time using microfluidics, Elena M. Lucchetta, Ji Hwan Lee, Lydia A. Fu, Nipam H. Patel, Rustem F. Ismagilov, Nature, vol. 434, Apr. 28, 2005.

A microfluidic culture platform for CNS axonal injury, regeneration and transport, Anne M. Taylor, Mathew Blurton-Jones, Seog Woo Rhee, David H. Cribbs, Carl W. Cotman, Noo Li Jeon, Nature Methods, vol. 2 No. 8, Aug. 2005.

Probing the role of multicellular organization in three-dimensional microenvironments., Dirk R. Albrecht, Gregory H. Underhill, Travis B. Wassermann, Robert L. Sah, Sangeeta N. Bhatia, Nature Methods, vol. 3, No. 5, May 2006.

nDEP microwells for single-cell patterning in physiological media, Nikhil Mittal, Adam Rosenthal and Joel Voldman, Lab Chip, 2007, 7, 1146-1153.

Cellular Immobilization within Microfluidic Microenvironments: Dielectrophoresis with Polyelectrolyte Multilayers, Samuel P. Forry, Darwin R. Reyes, Michael Gaitan, Laurie E. Locascio, J. Am. Chem. Soc. 2006, 128, 13678-13679.

Dielectrophoretic immobilization of cells within microfluidic microenvironments, Samuel P. Forry, Darwin R. Reyes, Michael Gaitan, Laurie E. Locascio, (No Date).

Dielectrophoretic registration of living cells to a microelectrode array, Darren S. Gray, John L. Tan, Joel Voldman, Christopher S. Chen, Biosensors and Bioelectronics 19 (2004).

Isolation of rare cells from cell mixtures by dielectrophoresis, Peter R.C. Gascoyne, Jamileh Noshari, Thomas J. Anderson, Frederick F. Becker, Electrophoresis 2009, 30, 1388-1398.

Micropatterning Neuronal Cells on Polyelectrolyte Multilayers, Darwin R. Reyes, Elizabeth M. Perruccio, S. Patricia Becerra, Laurie E. Locasio and Michael Gaitan, LAngmuir 2004, 20, 8805-8811.

Microfluidic Large-Scale Integration, Todd Thorsen, Sebastian J. Maerkl, Stephen R. Quake, Science, vol. 298, Oct. 18, 2002.

Subcellular positioning of small molecules, Shuichi Takayama, Emanuele Ostuni, Philip LeDuc, Keiji Naruse, Donald E. Ingber, George M. Whitesides, Nature, vol. 411, Jun. 128, 2001.

Retinoic Acid Induces Embryonal Carcinoma Cells to Differentiate into Neurons and Glial Cells, Elizabeth M. V. Jones-Villeneuve, Michael W. McBurney, Kem A. Rogers, and Vitauts I Kalnins, The Journal of Cell Biology, vol. 94, Aug. 1982, 253-262.

Neuronal Differentiation of P19 Embryonal Carcinoma Cells in Defined Media, M. Yao, G. Bain, and D,I. Gottlieb, Journal of Neuroscience Research 41:792-804 (1995).

Quantum Dot FRET-Based Probes in Thin Films Grown in Microfluidic Channels and supportive information, Georgeta Crivat, Sandra Maria Da Silva, Darwin R. Reyes, Laurie E. Locascio, Michael Gaitan, Nitsa Rosenzweig and Zeev Rosenzweig, J.Am. Chem. Soc. 2010, 132, 1460-1461.

Microfluidic Shear Devices for Quantitative Analysis of Cell Adhesion, Hang Lu, Lily Y. Koo, Wechung M. Wang, Douglas A. Lauffenburger, Linda G. Griffith and Klays F. Jensen, Analytical Chemistry, vol. 76, No. 18, Sep. 15, 2004.

Electrokinetic Bioprocessor for Concentrating Cells and Molecules, Pak Kin Wong, Che-Yang Chen, Tza-Huei Wang, and Chih-Ming Ho, Anal. Chem. 2004, 76, 6908-6914.

A scalable addressable Positive-Dielectrophoretic Cell-Sorting Array, Brian M. Taff and Joel Voldman, Anal. Chem. 2005, 77, 7976-7983.

Glutamate Receptor-Mediated Currents and Toxicity in Embryonal Carcinoma Cells, D.M. Turetsky, J.E. Huettner, D.I. Gottlieb, M.P. Goldberg, and D.W. Choi, Journal of Neurobiology, vol. 24, No. 9, pp. 1157-1169 (1993).

Isolation of Cultured Cervical Carcinoma Cells Mixed with Peripheral Blood Cells on a Bioelectronic Chip, Jing Cheng, Edward L. Sheldon, Lei Wu, Michael J. Heller, and James P. O'Connell, Anal. Chem. 1998, 70, 2321-2326.

Development of a Microchip-Based Bioassay System Using Cultured Cells, Makiko Goto, Kiichi Sato, Atsushi Murakami, Manabu Tokeshi and Tekehiko Kitamori, Anal. Chem. 2005, 77, 2125-2131.

\* cited by examiner

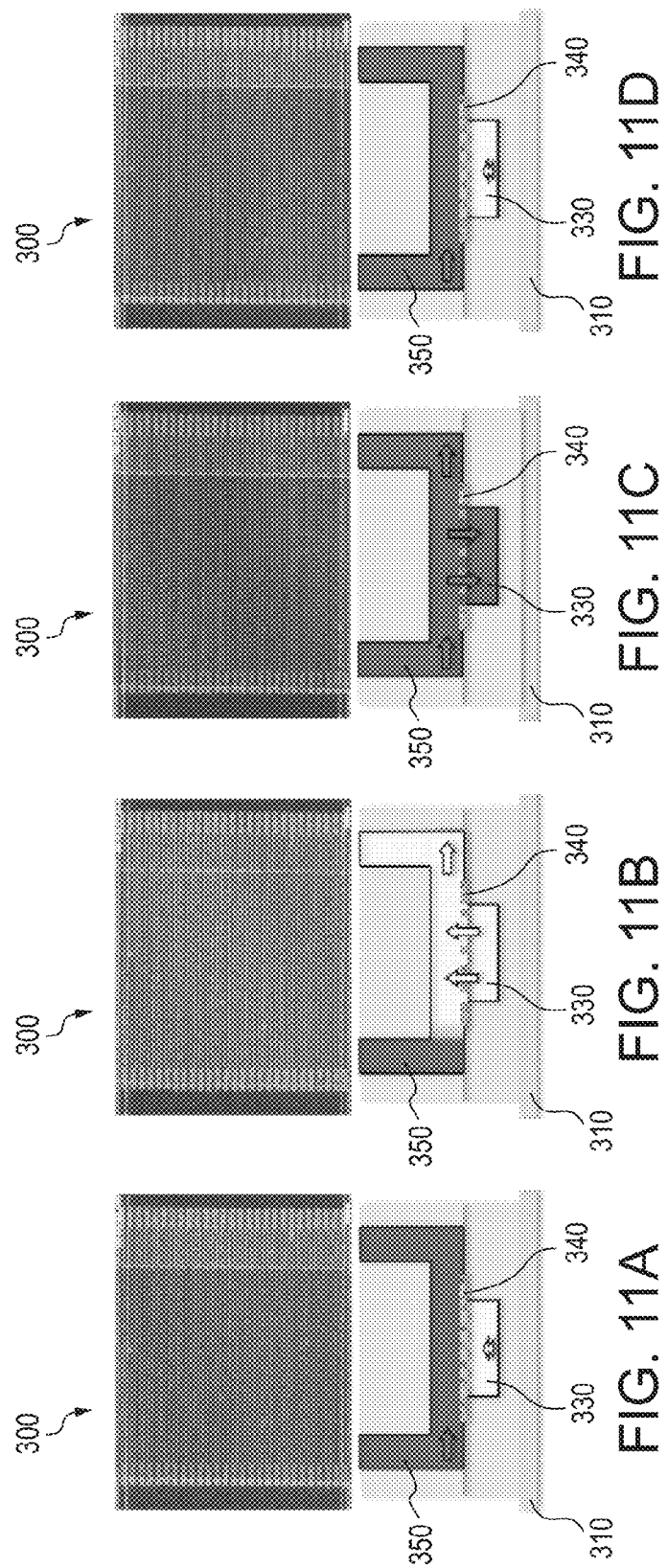

DIELECTROPHORETIC CELL CAPTURE

CROSS REFERENCES TO RELATED APPLICATIONS

This application claims priority upon U.S. provisional application Ser. No. 61/537,179 filed on Sep. 21, 2011.

FIELD

The present subject matter relates to components, compositions, systems, and methods for selectively capturing and retaining cells and bioparticles using dielectrophoresis.

BACKGROUND

The integration of tools for manipulating and controlling cells within microfluidic systems has steadily grown due to various unique features that microscale technologies can provide in terms of fine control over cellular microenvironments, flow conditions, and precise cell positioning for specific cell-cell interactions. The combination of such tools with microsystems has enabled the study of cellular processes that otherwise would not have been possible. Among the tools currently available to position cells in precise locations on a substrate is dielectrophoresis (DEP), which is an electrokinetic technique that can trap particles (e.g. cells) based on polarizability differences between the particle and the media in which the particles are suspended when both are exposed to a non-uniform field. The use of DEP has been primarily limited to, short-term manipulation studies of cells or preparative methods to separate cells from complex mixtures. Few studies have demonstrated DEP trapping for long term cell experiments where cell function still remains days after the trapping is effected. Therefore, it is of paramount importance, when developing DEP devices for in vitro cell studies, to demonstrate that cell viability and cell function (e.g., proliferation, motility, differentiation) are maintained after the electrokinetic manipulation.

A typical design for using DEP to trap cells is the placement of DEP electrodes under a fluid flow in a microfluidic device. This arrangement allows for increased trapping of cells in a short time and the removal of untrapped cells from non-DEP parts of a substrate surface. A challenge to this design is retaining the trapped cells in a fluid flow field at the selected positions when the DEP forces are removed. In order to produce DEP forces capable of moving cells up the field gradient, known as positive DEP (pDEP), cells must be suspended in sucrose or other low conductivity media. As opposed to cells suspended in high conductivity media (e.g. cell growth media), pDEP conditions produce stronger traps, thus attracting more cells and holding them on the substrate while the DEP forces remain active. The difficulty with this arrangement occurs when the DEP forces are switched off and the fluid flow field dislodges the positioned cells. In order to maintain the cells in position one needs to have good control over flow so that cells may attach through their integrins or other adhesive proteins over a period of time. An alternative to controlling the flow by pumps and valve systems is to have a "sticky" surface to which cells will anchor to, immediately after DEP trapping is achieved. By taking advantage of the extracellular molecules around the cells, such as antibodies or glycoproteins, either specific or non-specific binding can be effected. In turn, this can produce cell attachment on the pretreated surface via antibody/antigen binding or electrostatic interactions. The latter approach has been investigated using polyelectrolyte multiple layers (PEMs) as the surface coating material and has been shown to work when anchoring cells for short term experiments. However, a more relevant material is needed for in vitro long term cell experiments not only to facilitate cell anchoring, but also to maintain cell proliferation and cell function.

The present inventors have demonstrated cell patterning using PEMs when seeded in cell culture medium as well as when trapped under DEP conditions. Cells trapped under DEP and PEM conditions showed that over 93% of the cells remained anchored on the PEMs after the electrodes were de-energized. However, further research has been conducted in an attempt to extend the use of this approach for long term cell experiments. The results obtained using PEMs and DEP conditions show deleterious effects on the cells 24 hours after DEP cell trapping (see FIGS. 1A and 1B). Specifically, referring to FIGS. 1A and 1B, P19 cells attached onto PEMs are shown under different conditions. FIG. 1A illustrates P19 cells 24 hours after DEP trapping in a microfluidic channel. Cells were anchored on PEMs while in sucrose media, and then the sucrose was replaced with cell growth media. The faint vertical lines in the center are the indium tin oxide (ITO) electrodes used for DEP trapping. FIG. 1B illustrates P19 cells 24 hours after seeded on PEMs in cell growth media. Note the difference between P19 cells poorly attached in FIG. 1A versus well-attached healthy cells shown in FIG. 1B. The scale bar in FIG. 1A is 100 µm. Therefore, an alternative to this approach is needed to achieve long term cell experiments using a "sticky" surface and DEP.

The precise positioning of cells is a key requirement when utilizing microfluidic systems, specifically when cells are needed to be in defined areas for their stimulation and study. A number of approaches have been introduced to manipulate or capture cells within microchannels. These approaches vary from mechanical traps and flow control, to optical and electronic techniques. Among the electronic techniques, dielectrophoresis (DEP) has gained much attention in the microfluidics community. This phenomenon was first described by Pohl in 1951. However, it was not until the last decade that the number of publications increased significantly for applications including biosensors, medical diagnostics, particle filtration, nanoassembly, and DNA manipulation. The main advantages that DEP offers for particle manipulation include label free entrapment, simplicity of instrumentation, favorable scaling effects, the ability to apply repulsive (negative DEP) and attractive (positive DEP) forces, and the lack of microfabricated obstacles that distort the flow within the channels. DEP coupled with lab-on-a-chip devices have demonstrated suitability for DEP-based cell applications such as separation by size, sorting, focusing, filtration, trapping, and patterning.

In general, DEP electrodes have been patterned on solid substrates such as glass slides and silicon wafers. However, few previous efforts have investigated patterning electrodes, for purposes other than DEP, onto permeable surfaces. For example, Duan and Meyerhoff showed that metallization of permeable membranes was possible and used patterned nylon membranes for sandwich enzyme immunoassays. Later, Švorčik et al. characterized the sputtering process to metallize polyethylene terephthalate (PET).

SUMMARY

The difficulties and drawbacks associated with previously known technology are addressed in the present compositions, assemblies and methods for capturing bioparticles.

In one aspect, the present subject matter provides a layered composition for capturing bioparticles during dielectrophoresis (DEP). The layered composition comprises at least one layer of an adhesion material (i.e. extracellular matrix), and a layer of a polycation material disposed on the at least one layer of the adhesion material. The layer of the polycation material provides an exposed face for capturing bioparticles during dielectrophoresis.

In another aspect, the present subject matter provides a layered assembly for use in dielectrophoresis (DEP). The assembly comprises a polyester permeable membrane defining an outer face, at least one electrically conductive member disposed on the outer face of the membrane, and a layered composition disposed on at least one of the outer face of the membrane and the at least one electrically conductive member. The layered composition includes (i) at least one layer of an adhesion material, and (ii) a layer of a polycation material disposed on the at least one layer of the adhesion material.

In still another aspect, the present subject matter provides a method for retaining bioparticles along a target surface during dielectrophoresis (DEP). The method comprises providing a system for performing dielectrophoresis including provisions for generating a non-uniform electric field proximate the target surface. The method also comprises applying a layered composition on the target surface. The layered composition includes (i) at least one layer of an adhesion material and (ii) a layer of a polycation material disposed on the at least one layer of the adhesion material. The layer of the polycation material provides an exposed face for retaining bioparticles. The method additionally comprises performing dielectrophoresis such that bioparticles contact the exposed face of the layered composition on the target surface, whereby the bioparticles are retained on the exposed face of the layered composition at the target surface.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

FIG. 11A illustrates another microfluidic device in accordance with the present subject matter and a schematic illustration of two fluids flowing in the device.

FIG. 11B illustrates the device of FIG. 11A and two fluids flowing in the device.

FIG. 11C illustrates the device of FIG. 11A and two fluids flowing in the device.

FIG. 11D illustrates the device of FIG. 11A and two fluids flowing in the device.

DETAILED DESCRIPTION OF THE EMBODIMENTS

Hybrid Cell Adhesive Materials

Figure 1A:
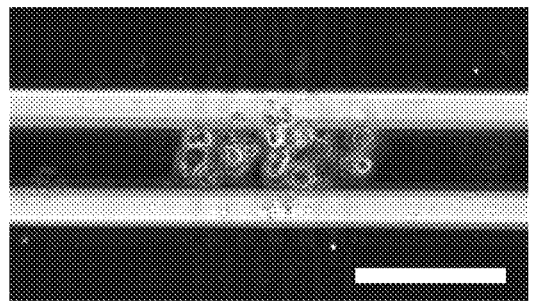
FIG. 1A illustrates a prior art technique of trapping P19 cells in a microfluidic channel using DEP after 24 hours.
Figure 1B:
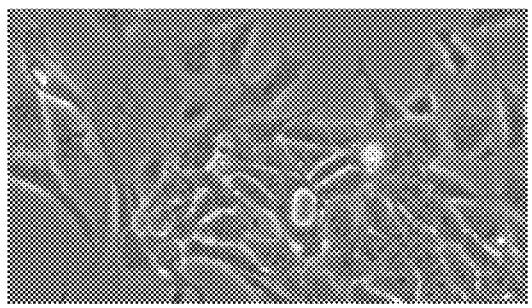
FIG. 1B illustrates healthy P19 cells seeded on PEMs in cell growth media after 24 hours.

Dielectrophoresis (DEP) for cell manipulation has primarily focused on approaches for separation/enrichment of cells of interest. Advancements in cell positioning and immobilization onto substrates for cell culture, either as single cells or cell aggregates, has benefited from the intensified research efforts in DEP (electrokinetic) manipulation. However, there has yet to be a DEP approach that provides the conditions for cell manipulation while promoting cell function processes such as cell differentiation.

In accordance with the present subject matter, a system is provided that combines DEP with a hybrid cell adhesive material (hCAM) to allow for cell entrapment and cell function, as demonstrated by cell differentiation into neuron-like cells (NLCs). The hCAM, comprised of polyelectrolytes and fibronectin (FN), is adapted to function as an instantaneous cell adhesive surface after dielectrophoretic (DEP) manipulation, and to support long term cell function (cell proliferation, induction, and differentiation). Pluripotent P19 mouse embryonal carcinoma cells flowing within a microchannel were attracted to the DEP electrode surface and remain adhered onto the hCAM coating under a fluid flow field after the DEP forces were removed. Cells remained viable after DEP manipulation for up to 8 days, during which time the P19 cells were induced to differentiate into NLCs. This approach could have further applications in areas such as cell-cell communication, three-dimensional cell aggregates to create cell microenvironments, and cell co-cultures. Although the present subject matter and its various embodiments are primarily described with regard to cells, it will be understood that the subject matter is applicable to a wide array of bioparticles.

The term "bioparticle" as used herein refers to any material shed from an organism and is typically biological in nature. The bioparticles can be classified according to any of the general biological classes of materials. For example, the bioparticle can be proteinaceous (e.g., a protein, peptide, or antibody), nucleic acid-containing (e.g., a nucleobase, nucleotide, oligonucleotide, or nucleic acid), lipid-containing (e.g., fatty acid-containing), steroidal, one or more small biological molecules, other types of biological material, and combinations thereof. Some more specific examples of bioparticles include cells (e.g., skin-derived or epidermis cells), protein structures, hair, pathogenic and non-pathogenic bacterial, viral, fungal, protozoal or other organisms, and plant-derived material (e.g., pollen). Shed material from the skin is particularly plentiful and includes particles from the outer skin layer (e.g., stratum corneum) and other skin layers that contain keratin. Though the bioparticles are largely organic, they may also be inorganic. For example, the bioparticle can be a mineral, such as talc. The bioparticle also need not be natural in composition, but may be synthetic (e.g., particulates used in cosmetics or other toiletries). Often, the bioparticles are constructed of aggregations of molecules or other bioparticles. Such aggregations include cells, viruses, pollen grains, skin flakes, hair, bacteria, and several other types of aggregations of organic and inorganic molecules.

In accordance with the present subject matter, the effects of different cell adhesive materials on the attachment and function of P19 cells were assessed to determine the most appropriate surface on which to investigate cell function (specifically differentiation) after DEP trapping and subsequent removal of the electric field. P19 cells are a pluripotent cell line that have the ability to differentiate through several pathways in vitro, specifically neuronal, cardiac muscle and skeletal muscle. The ability of P19 cells to differentiate after DEP manipulation would demonstrate the successful generation of a cell adhesive material that allows long term culture. This is critical for performing experiments with cells that are arranged by DEP. The present subject matter demonstrates that an hCAM prepared from FN and a poly(allylamine hydrochloride) (PAH) layer on top of PEMs allowed for instantaneous cell anchorage after DEP trapping. Furthermore, long term cell viability (more than a week) and differentiation were also attained, thus demonstrating the utility of the hCAM for long term in vitro cell experiments.

In accordance with the present subject matter, two sets of separate investigations were performed to identify a biocompatible coating that allows P19 cell adhesion and growth under the low conductivity media sucrose and under electric fields. Tissue culture polystyrene (TCPS), polystyrene (PS) (spin coated plasma oxidized), cell culture media (CCM) pretreated PS, poly-L-lysine, $(PAH/PSS)_2PAH$, collagen I (Col I), and fibronectin (FN) were evaluated as adhesion substrates for cells suspended in sucrose for 15 min, the maximum time typically required for DEP positioning of cells. The assessments described herein were based on counting the number of adhered cells remaining on the surface and counting the fraction of rounded cells (quantitative cell morphology assessment) as well as qualitative evaluation of cell morphology versus the morphology of the cells on the TCPS substrate 24 hours after cell seeding. Previously, it was found that PEMs were able to capture cells trapped with DEP forces, but the compatibility of PEMs for long term cell culture was not evaluated. The data indicated that the cells adhered well to the $(PAH/PSS)_2PAH$ when the cells were seeded in cell culture media (700 cells/mm$^2$). But when the cells were seeded in sucrose, fewer than 9 cells/mm$^2$ were observed. Cell seeding in sucrose significantly decreased the number of adhered cells on collagen, PAH, spin coated PS with plasma treatment and fibronectin. Sucrose did not appear to influence adhesion on poly-lysine and TCPS surfaces. Because it was found that sucrose did not appear to decrease cell function when used in tissue culture polystyrene, it was hypothesized that sucrose may decrease the adhesive nature of the substrate by blocking or removing the proadhesive molecules. During the substrate evaluation, it was noted that although cells remain adhered to collagen I and poly-lysine after 24 h, greater than 40 and 80 percent of the cells were rounded and appeared unhealthy. Qualitative evaluation of the morphology suggested that the P19 cells that remained adhered to the FN substrate had a spread appearance similar to the cells on the TCPS dish. Overall, the data from this evaluation suggested that the FN substrate best supports growth of the P19 cells when they are seeded from a sucrose solution.

Figure 2A:
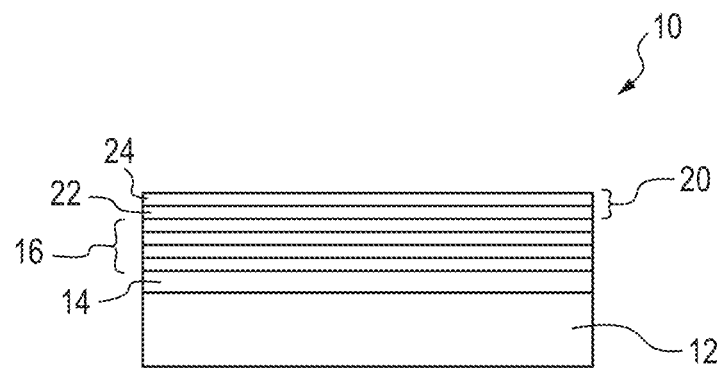
FIG. 2A is a schematic cross sectional illustration of a glass slide assembly in accordance with the present subject matter.
Figure 2B:
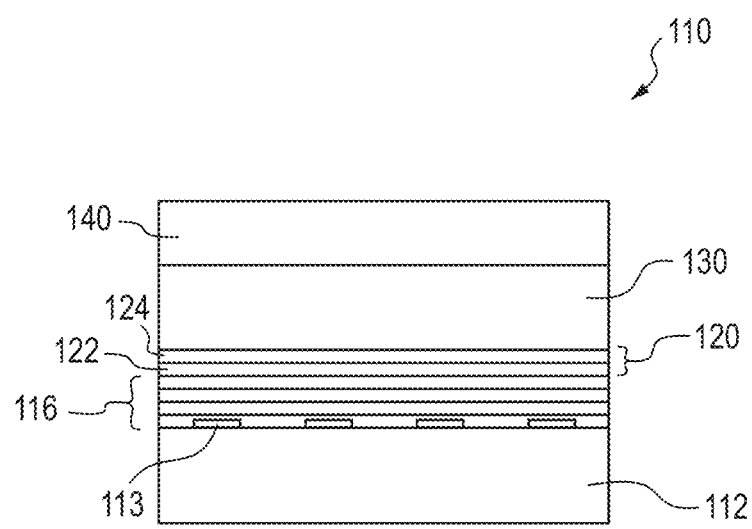
FIG. 2B is a schematic cross sectional illustration of a flow device in accordance with the present subject matter.

Additional assessments showed that when trapping P19 cells under a continuous flow field using DEP and FN-coated substrates, all the cells detached at the moment the DEP forces were stopped. To take advantage of the ability of FN to promote long term adhesion and growth of the P19 cells and the PEMs that support capture of cells after DEP forces are applied, an hCAM composition was prepared from FN, PEMs, and a PAH layer on top of the FN. A schematic of the hybrid material and utilized in two layered systems is shown in FIGS. 2A and 2B. The combination of FN adsorbed to PEMs (negatively charged PSS as the outermost layer) and PAH on top of the FN was tested for cell adhesiveness under DEP conditions and long term cell viability. The cell adhesiveness of the hCAM was assessed first under cell seeding conditions in sucrose. Silanized coverslips were polystyrene coated and then plasma oxidized before depositing the layers of the polyelectrolytes (see FIG. 2A). The procedure to deposit the hCAM was similar for the experiments carried out on the DEP electrodes (see FIG. 2B), differing only in the PEMs being directly deposited on the ITO/glass surface and not on a polystyrene layer. Specifically, a schematic side view of a glass coverslip assembly 10 is shown in FIG. 2A and a DEP device 110 is shown in FIG. 2B, both with the hCAM deposited on top. The assembly 10 in FIG. 2A comprises a glass substrate 12, a layer of polystyrene (PS) 14 disposed on the glass substrate, a collection of PEMs 16 disposed on the layer of polystyrene, and a layer 20 of the hCAM material disposed on the collection of PEMs. The PEMs 16 are depicted as including four (4) layers, but it will be understood that a greater number or lesser number of layers could be utilized. The layer 20 of hCAM material includes an underlayer 22 of FN and an outerlayer 24 of PAH disposed on the underlayer 22. The flow device 110 and particularly, a microfluidic flow device, generally comprises a glass substrate 112, two or more electrically conductive electrodes 113 such as indium tin oxide (ITO) electrodes, a collection of PEMs 116 disposed on the glass substrate 112 and the one or more electrodes 113, and a layer 120 of the hCAM material. The hCAM material typically includes an underlayer 122 of FN and an outerlayer 124 of PAH disposed on the underlayer 122. The device 110 also includes a flow channel 130 which is generally defined by one or more walls 140 formed from a suitable material such as polydimethyl siloxane (PDMS). The hCAM is comprised of a layer of FN and PAH on top of four layers of polyelectrolytes (PAH/PSS)$_2$, which in turn were deposited onto polystyrene-coated coverslips as in FIG. 2A and ITO electrodes as in FIG. 2B. The microchannel is molded in PDMS and reversibly bound onto the device.

Figure 3A:
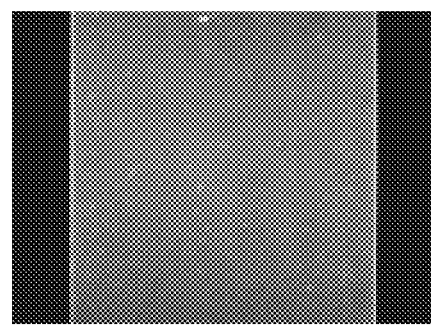
FIG. 3A is an image of a layer of PAH-FITC on a collection of PEMs.
Figure 3B:
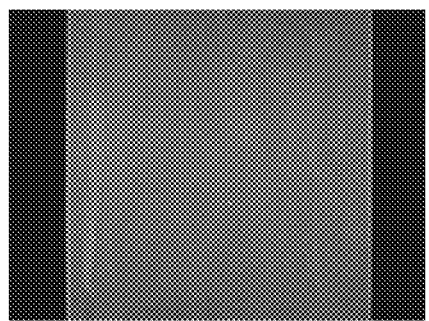
FIG. 3B is an image of a layer of FN-ROX on a collection of PEMs.
Figure 3C:
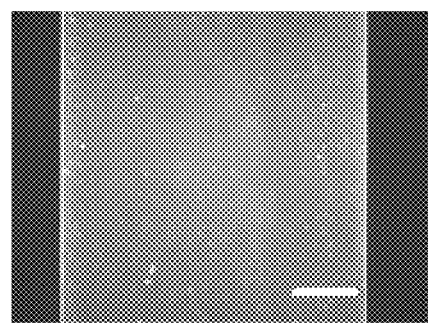
FIG. 3C is an image of PAH-FITC deposited on FN-ROX, and both deposited on PEMs.

The hCAM was examined by depositing fluorescently labeled FN and PAH in microfluidic channels and imaging the channels using fluorescence microscopy as shown in FIGS. 3A-3C. Specifically, images of fluorescently labeled components of the hCAM are shown in FIGS. 3A-3C. FIG. 3A shows PAH-FITC and FIG. 3B shows FN-ROX deposited on four layers of polyelectrolytes ((PAH/PSS)$_2$). FIG. 3C shows PAH-FITC deposited on FN-ROX, and both on (PAH/PSS)$_2$. The interior region in FIG. 3C denotes the overlapping of the labeled PAH and FN throughout the surface. The scale bar in FIG. 3C is 200 µm. Fluorescently labeled FN (FN-ROX) and PAH (PAH-FITC) were deposited separately (FIG. 3A and FIG. 3B) and then together with PAH-FITC on top of FN-ROX, and in all cases they were deposited on top of 4 layers of polyelectrolytes ((PAH/PSS)$_2$). All the images in FIGS. 3A-3C were taken after the channels were rinsed and then refilled with PBS. The fluorescence from PAH-FITC on (PAH/PSS)$_2$ is shown in FIG. 3A. In FIG. 3A, it was determined that PAH-FITC homogenously coats the surface. FIG. 3B shows FN-ROX bound to (PAH/PSS)$_2$. In FIG. 3B, it was determined that the FN-ROX, also covers the surface of the channel. FIG. 3C shows PAH-FITC deposited onto FN-ROX, which was first deposited on (PAH/PSS)$_2$. In FIG. 3C, the darker regions (excluding the edges) indicate the areas where there is a thin layer of the materials, whereas the lighter areas are observed at the edges of the channel where more accumulation of the deposited PEMs was previously observed. The PBS rinse was performed by aspirating from the outlet reservoir using a vacuum pump. The fluorescence intensities remained constant after rinsing, suggesting that the hybrid layer is stable in a fluid flow field.

Figure 4A:
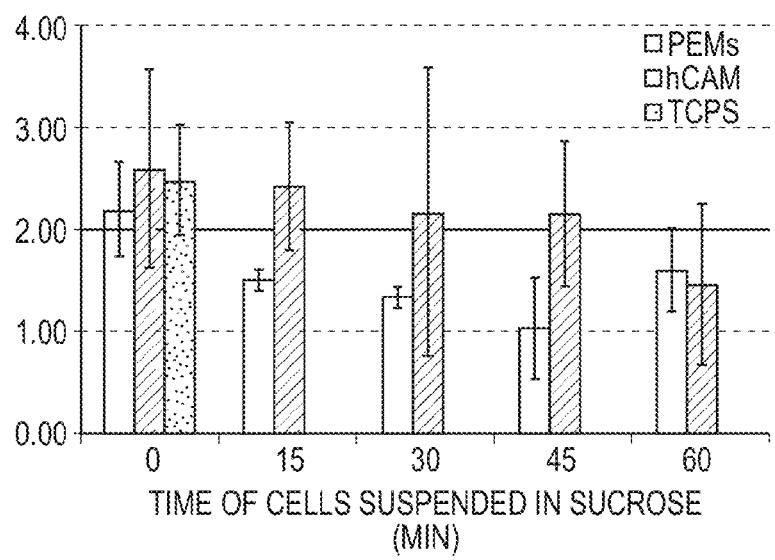
FIG. 4A is a graph showing the change in the number of cells seeded in sucrose media after 24 hours and exposed to PEMs, hCAM, and TCPS.

Additionally, the proliferation and viability of P19 cells seeded in sucrose on the hCAM surface were assessed. FIG. 4A shows the change in the number of cells seeded in sucrose media after 24 h. The cells were exposed to sucrose media for 0 min, 15 min, 30 min, 45 min, and 60 min, after which cell culture media (CCM) was added to the well to substitute the sucrose media. This plot shows a tendency of the hCAM to allow for similar levels of cell proliferation, specifically, cell doubling (see the crosshatched bars in FIG. 4A) at all time points. The doubling value was calculated by dividing the number of cells at 24 hours by the number of cells seeded at 0 h. A value of 2 is expected if the number of cells doubled. Cells exposed to CCM only (0 minutes in sucrose) and sucrose for 15 min, 30 min, and 45 minutes showed the best results for the hCAM surface. Only the 60 minutes sample, on the hCAM showed a value of less than 2. On the other hand, the cells seeded on PEMs do not exhibit cell doubling except for those that were seeded in CCM (0 minutes in sucrose). The average doubling value obtained for P19 cells seeded in sucrose on the hCAM and on PEMs were 2.06±0.41 and 1.38±0.25, respectively. These results demonstrate the compatibility of the hCAM with DEP conditions (sucrose media), which is critical to successfully generate DEP trapping forces that will hold cells in place. The PEM alone, on the other hand, was incapable of promoting P19 cell attachment and proliferation (cell doubling) when cells were suspended in sucrose.

Figure 4B:
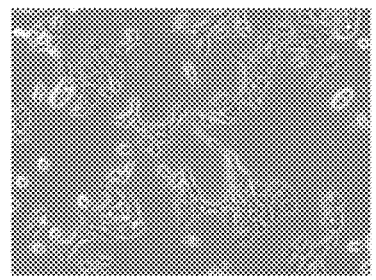
FIG. 4B is an image showing P19 cells 24 hours after seeding on TCPS.
Figure 4C:
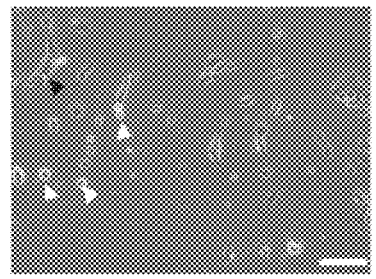
FIG. 4C is an image showing P19 cells 24 hours after seeding on PEMs.
Figure 4D:
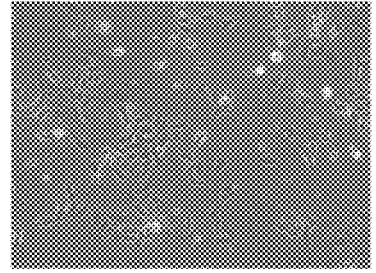
FIG. 4D is an image showing P19 cells 24 hours after seeding on hCAM.

P19 cell morphology after 24 hours was also evaluated, in which FIGS. 4B-4D show P19 cells 24 hours after seeding on TCPS, PEMs, and hCAM, respectively. These images show P19 cells that were not exposed to sucrose (FIG. 4B) and cells that were exposed to sucrose (FIGS. 4C and 4D) for 15 minutes and later replaced with CCM. The morphology of the P19 cells was affected by sucrose exposure and the surface on which they were plated. Cells on PEMs appeared more rounded, indicating weak attachment to the surface of the PEMs (see white arrow heads in FIG. 4C). In some cases they formed elongated structures larger than the average surface area of the cells (see black arrowhead in FIG. 4C). Conversely, P19 cells on hCAM showed similar morphology to the cells seeded in CCM on TCPS and similar doubling values (doubling value=2.5 on TCPS versus 2.6 on hCAM). Specifically, FIGS. 4A-4D are directed to proliferation of P19 cells seeded on PEMs and hCAM after resuspension in sucrose. FIG. 4A shows the change in the number of cells seeded in sucrose media after 24 hours (doubling value). Values are approximately 2 for cells on the hCAM surface, whereas cells on PEMs show values of less than 2 when cells were suspended in sucrose (averages of 89 cells/frame, 44 cells/frame, and 25 cells/frame were observed for TCPS, PEMs, and hCAM, respectively; error bars represent one standard deviation). FIG. 4B shows representative phase contrast images of P19 cells on TCPS, PEMs (FIG. 4C), and on hCAM (FIG. 4D) 24 hours after seeding. Cells on PEMs and hCAM were suspended in sucrose for 15 min. Black arrowhead in (FIG. 4C) indicates cell with larger than average surface area, and white arrowheads indicate weak cell attachment to the surface of the PEMs. The scale bar in FIG. 4C is 100 µm.

Figure 5:
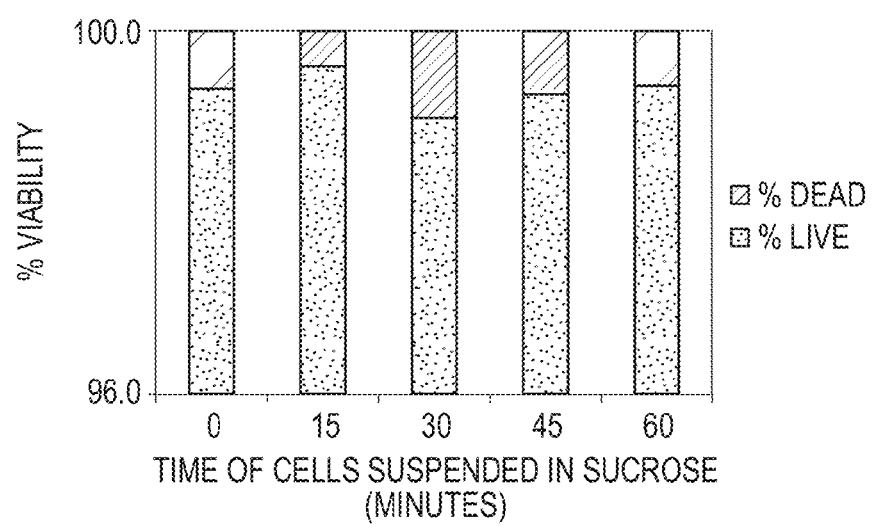
FIG. 5 is a graph of percent viability of P19 cells on the hCAM composition of the present subject matter.

The viability of P19 cells was assessed using a live/dead viability assay from Invitrogen Corp. The viability results in FIG. 5 show that 99% or more of the cells were viable 48 hours after cell seeding on hCAM, and 96% of the cells were viable on the PEMs. Also, the results indicate that P19 cells can be exposed to sucrose for at least 60 minutes with no significant change in viability. Specifically, FIG. 5 illustrates percent viability of P19 cells on the hCAM. Cells are 99% viable or more at all sucrose exposure times. The percentage of live cells is represented by the gray color bars, whereas the dead cells (cross hatched bars) complete the 100% of the cells in each bar with ≤1% dead cells.

Figure 6A:
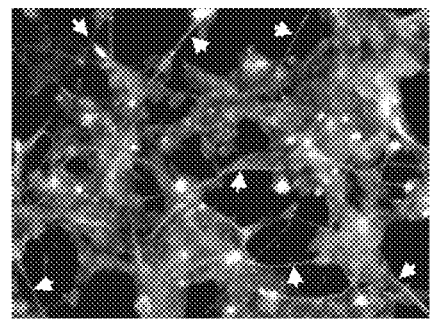
FIG. 6A is an image of P19 cells on adhesive TCPS.
Figure 6B:
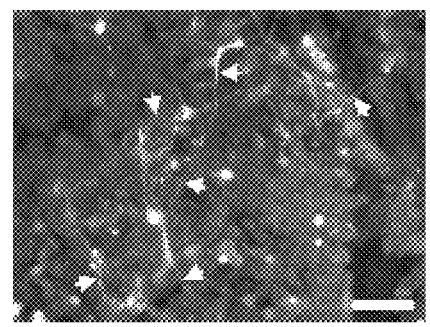
FIG. 6B is an image of P19 cells on $(PAH/PSS)_2$ FN.
Figure 6C:
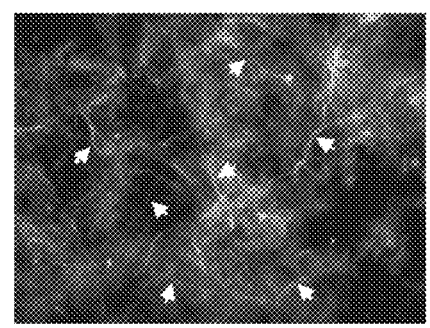
FIG. 6C is an image of P19 cells on hCAM.

To fully evaluate the function of P19 cells after 15 minutes of sucrose exposure, adhered P19 cells on TCPS (control, no sucrose exposure), (PAH/PSS)$_2$/FN, and hCAM were differentiated. Cell differentiation was evaluated using a procedure that was modified from previous reports on P19 cell differentiation. The present process allows for the plating of dissociated cells on adhesive surfaces and induction of differentiation after cell attachment on the substrates. Cell differentiation was carried out by first exposing P19 cells to sucrose for 15 min, exchanging the sucrose for low serum/retinoic acid induction media and after 4 days exchanging the low serum media for normal cell growth media. FIG. 6A shows an image of immunostained P19 cells that were induced to differentiate on adhesive TCPS without exposure to sucrose. Neurofilaments and neurofilament proteins in the cytoplasm of the NLCs are stained with a neurofilament antibody. Neurofilaments are observed as cables connecting the cells, and the arrowheads point at neurofilaments generated by the P19 cells, which differentiated into NLCs. FIGS. 6B and 6C show P19 cells differentiated on (PAH/PSS)$_2$FN and on the hCAM, respectively. Each image shows the clear formation of neurofilaments after P19 cells were induced and differentiated on the surfaces. This indicates P19 cells can be induced to become NLCs and form neurofilaments even when the cells are fully adhered onto these substrates during the programming and induction process. Specifically, FIGS. 6A-6C show immunofluorescence images of differentiated P19 cells induced on TCPS (FIG. 6A), on (PAH/PSS)$_2$FN (FIG. 6B), and the hCAM (FIG. 6C). Neurofilaments were immunostained, demonstrating neuronal differentiation (see arrows). Induction and differentiation were possible while cells were adhered on all surfaces. The scale bar in FIG. 6B is 50 µm.

Figure 7:
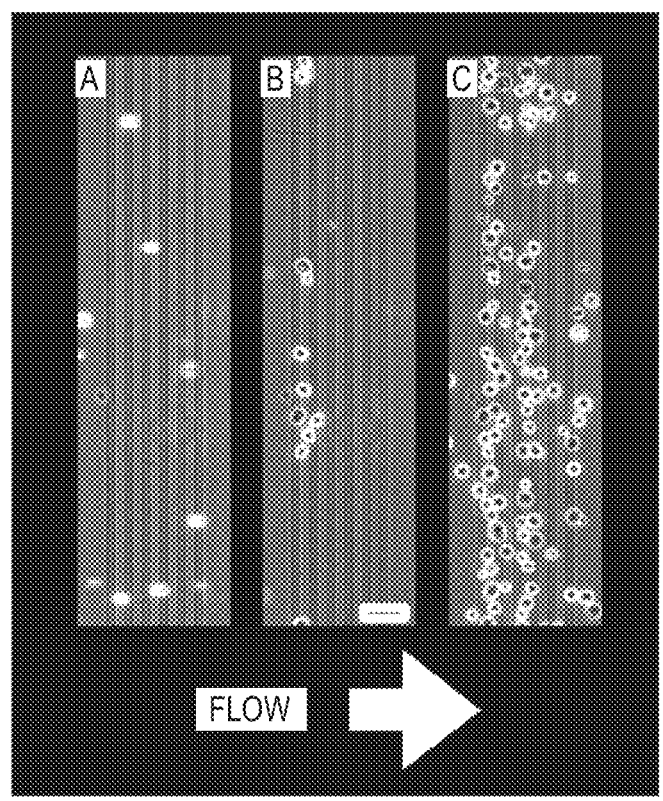
FIG. 7 illustrates DEP trapping of P19 cells on hCAM.

As previously described, previous attempts to use PEMs for long term cell experiments demonstrated that polyelectrolytes alone did not maintain cell viability after exposure to DEP conditions (sucrose and electric fields). The hybrid surface of the present subject matter, hCAM, showed the ability to accommodate long term P19 cell growth and function after the surface and the cells were exposed to sucrose. Once it was determined that the hCAM could support long term cell function, the engineered material was used with a DEP device and all conditions used for such experiments. The combination of polyelectrolytes and FN on the ITO electrodes produced a surface suitable for DEP-based cell anchorage, proliferation, and differentiation as shown in FIGS. 7 and 8. FIG. 7 shows a sequence of cell movement in a fluid flow field and the application of DEP forces.

Specifically, FIG. 7 illustrates DEP trapping of P19 cells on hCAM. Panel A shows P19 cells flow down the channel passing over the DEP ITO electrodes (vertical dark gray lines) without being trapped. The ITO electrodes were initially off for a few seconds before they were turned on. As shown in panel B, once the electrodes were turned on, P19 cells were trapped by the DEP forces and then anchored onto the hCAM. Panel C shows ITO electrodes were turned off, and P19 cells trapped on the surface remained adhered to the hCAM even while exposed continuously to a fluid flow field. The scale bar in Panel 7B is 50 µm. More specifically, Panel A in FIG. 7 shows a phase contrast image where P19 cells are flowing down the channel (left to right) in the absence of DEP. The cells are passing over the electrodes without being trapped. The first cells trapped when the DEP forces are active are shown in Panel B of FIG. 7. The applied voltage was varied throughout the investigation from 7 V to 3 V at a frequency of 30 MHz (electric fields between 7,000 V/cm to 3,000 V/cm) in order to start trapping cells on the first pair of electrodes and later cell trappings on subsequent electrodes as the voltage was lowered. Panel C in FIG. 7 shows the P19 cells trapped at the end of the DEP experiment when voltage is no longer being applied. Cells remained trapped under the fluid flow field without an electric field present.

Figure 8A:
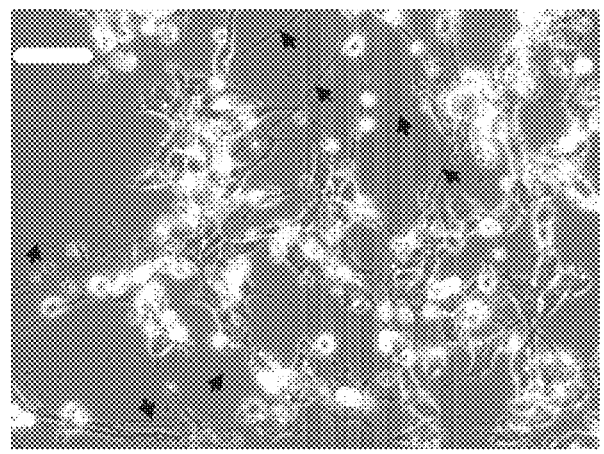
FIG. 8A is an image of P19 cell differentiation after DEP trapping.
Figure 8B:
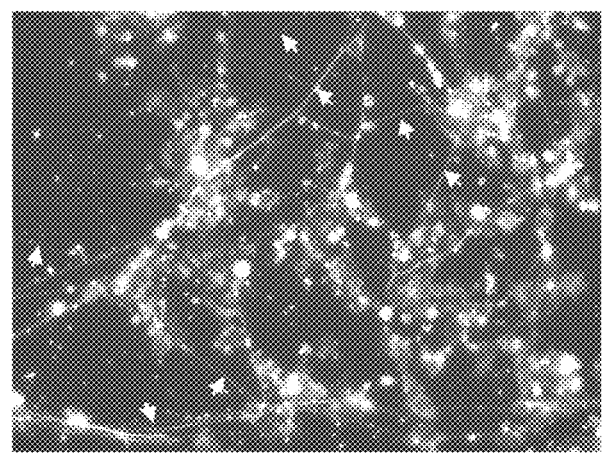
FIG. 8B is an image of P19 cell differentiation after DEP trapping and 8 days in culture.

Cells that were trapped under DEP conditions on the hCAM surface in a fluid flow field were later induced to differentiate into NLCs. FIGS. 8A and 8B illustrate P19 cell differentiation after DEP trapping and 8 days in culture in a microfluidic system. The phase contrast image (FIG. 8A) shows a number of neurofilament projections connecting the cells once they have differentiated (see arrowheads), which is indicative of successful P19 cell differentiation into NLCs. The ITO electrodes can be seen (gray vertical lines) in the images where cells grew out after initial trapping. Cell migration away from the electrode occurred during the 6 days (2 days in CCM and 4 days in induction media) required for differentiation.

Immunostaining of neurofilaments better illustrates the complexity of the interconnections among the cells. The fluorescence image in FIG. 8B more prominently shows the projections P19 cells produced after the differentiation process. The presence of stained neurofilament processes and staining in the cytoplasm of NLCs confirms the suitability of the hCAM as a surface that provides for the anchorage of P19 cells under DEP conditions in microfluidics (sucrose media, electric fields, and fluid flow field), and that simultaneously allows the cells to function properly in their ability to differentiate after the complete process.

Specifically, FIGS. 8A and 8B depict differentiated P19 cells within a microchannel after DEP trapping and induction. FIG. 8A shows phase contrast image of NLCs (differentiated P19 cells) on the hCAM after 8 days in the microfluidic system. The vertical dark gray lines are the ITO electrodes used to trap the cells on day 1. Arrowheads point to the projections of differentiated P19 cells. FIG. 8B shows immunostaining of neurofilaments, a marker of neuronal cells and therefore indicative of successful differentiation of the P19 cells, illustrates the projections from differentiated cells throughout the surface of the device. Cells on the ITO electrodes as well as cells that proliferate away from the electrode regions differentiated equally. Arrowheads point to the neurofilaments formed during cell differentiation. The scale bar in FIG. 8A is 50 µm.

In the subject matter described herein, an engineered cell adhesive surface was demonstrated with a two-fold purpose: the anchorage of cells under DEP conditions with continuous fluid flow field and its ability to support long term cell experiments such as cell induction and differentiation. A hybrid material comprising polyelectrolytes and FN, with FN and PAH at the surface satisfied this goal. The P19 cells were trapped with DEP forces and anchored on the hCAM surface in a continuous flow field within a microfluidic system. The cells were viable for up to 8 days and were able to undergo neuronal differentiation until cell fixation was carried out for immunostaining purposes. Additionally, the ability to induce P19 cells while the cells are adhered to a surface was demonstrated. This suggests that neurodevelopment studies that assess cell-cell interactions could be performed in microfluidic devices with hCAM surfaces. Going forward, microfluidics may allow the study of cell-by-cell mechanisms, including the pattern of morphogen response tracked by assessing the fraction of cells that have differentiated. This type of study may be possible by integrating DEP investigation systems with controlled microfluidic laminar flows.

Thus, in accordance with the present subject matter, a hybrid cell adhesive material, i.e. hCAM, comprises an outermost layer of one or more polycation or polyelectrolyte materials disposed on a layer of fibronectin (FN) or other extra cellular matrix material. The hCAM layer captures cells or other bioparticles by attraction from dielectrophoretic forces, and retains the cells in place along an exposed surface of the hCAM layer. The hCAM layer uses the polycation material(s) to electrostaticallly bind the cells instantaneously which have a net negative charge along their surface, while concurrently the fibronectin or other extracellular matrix material promotes long term survival of the retained cells.

A wide array of polycation materials can be used in addition to, or instead of, poly(allylamine hydrochloride) (PAH) such as but not limited to poly(ethylene imine) (PEI), poly (diallyl-dimethyl ammonium) chloride (PDADMAC), poly (lysine), polyacrylamide (PAAm), similar agents, and combinations thereof.

A wide array of extracellular matrix materials can be used in addition to, or instead of, fibronectin such as laminin; elastin; collagen; collagen fibrils; proteoglycons such as heparan sulfate, chondroitin sulfate and the like; hyaluronic acid; and any other natural or synthetic material that will promote cell adhesion and can be assembled in layer-by-layer techniques referred to herein as an extracellular matrix material analogue. Combinations can also be used.

Preferably, the layers of the hCAM material, i.e. layer(s) of polycation material(s) and layer(s) of adhesion material(s) (i.e. extracellular matrix), are assembled in a layer-by-layer technique. The term "layer-by-layer" as used herein refers to a strategy by which layers of materials, usually polymers, are stacked one on top of each other by adsorption, and beginning on a substrate. Typically, electrostatic forces keep the layers adsorbed to the substrate initially and then to one another. However, other interactions have been shown to maintain or at least assist in maintaining the multilayers assembled as a single film or layer. Examples of these other interactions include covalent bonds, hydrogen bonding, donor-acceptor interactions, and the like. Generally, if the materials of the hCAM are merely mixed or otherwise combined, an undesirable precipitate typically forms.

The hCAM can utilize particular concentrations of agents in each of the layers. When using fibronectin as the extracellular matrix (adhesion) material, a preferred concentration is from about 25 to about 50 µg/ml, based upon the total amount of the FN-containing layer. When using PAH or other similar polycation material, a preferred concentration of the PAH or like material is typically about 1 mg/ml, based upon the total amount of the polycation layer.

The hCAM can optionally include one or more other agents, components, and/or materials for example polyions and lipids. Moreover, the present subject matter contemplates the potential use of particular combinations such as fibronectin/heparan sulfate, fibronectin/chondroitin sulfate, laminin/heparan sulfate, and laminin/chondroitin sulfate.

Additional nonlimiting examples of agents that could be included in the hCAM are growth factor peptides and proteins, small molecule drugs, i.e. which are slowly released during cell adhesion and growth, nano materials, antibodies (which influence cell response, fluorescent probes, i.e. for monitoring degradation of the extracellular matrix material, and combinations thereof. Typical concentrations of these agents in the hCAM are from about 5 µg/ml to about 100 µg/ml.

The total thickness of the hCAM after deposition depends upon the number of layers, and the distance of the cells to be trapped or retained on the hCAM layer from the substrate. Typically, at least one or more underlying layers are provided on the substrate and are disposed between the substrate and the hCAM. Typically, only one layer of the extracellular matrix material, e.g. fibronectin is needed. That layer should be close enough to the outer exposed surface of the hCAM to support cell survival and growth. Although not wishing to be bound to any particular theory, the thickness of the extracellular matrix material, e.g. fibronectin, is generally from about 2 nm to about 5 nm. The thickness of the polycation layer, after drying is typically about 2 nm for each layer. Thus, for an assembly of four (4) layers of polyions/fibronectin/PAH, the total thickness is generally about 12 nm to about 15 nm.

Polyester Membranes

In accordance with the present subject matter, a new system for dielectrophoretic cell capture on permeable polyester membranes is provided. Photolithographic techniques were used to fabricate gold microelectrodes on a polyester membrane. The characterization of the microelectrodes showed that there were no differences regarding roughness, permeability, and hydrophilicity of the membrane before and after processing. Finally, dielectrophoretic cell capture and viability in a microfluidic device was demonstrated on the patterned membrane. These membranes could ultimately be combined with multilayer microfluidic devices to form a powerful tool for studies of cell-cell interactions in co-culture, whereby spatial separation of different cell types and/or microenvironments are required.

A multilayer microfluidic device with a PET membrane has been used to separate the channels for cell culture and cell manipulation to monitor the induced gene expression of ZsGreen1-DR. The use of permeable PET membranes in multilayer microfluidic devices has several advantages. Soluble factors could diffuse through the intermediate membrane, and their effect on the cells could be observed without disturbing influences caused by their supply. Additionally, the double layered design adds another level of temporal and spatial control. The combination of a multilayer microsystem with dielectrophoretic cell capturing onto a permeable membrane will enable in vitro co-culture systems closer to cell-cell interactions that occur in vivo.

In accordance with the present subject matter, the fabrication, characterization, and use of a DEP microfluidic device comprised of electrically conductive, e.g. gold, microelectrodes on a permeable PET membrane is provided. Photolithographic procedures along with other techniques are used to evaporate and lift-off gold on PET membranes to obtain patterns of interdigitated electrodes. These electrodes were characterized using atomic force microscopy (AFM), scanning electron microscopy (SEM), and optical microscopy. The electrodes were tested for dielectrophoretic cell capture, and cell viability on the gold and PET membrane surfaces.

Figure 9:
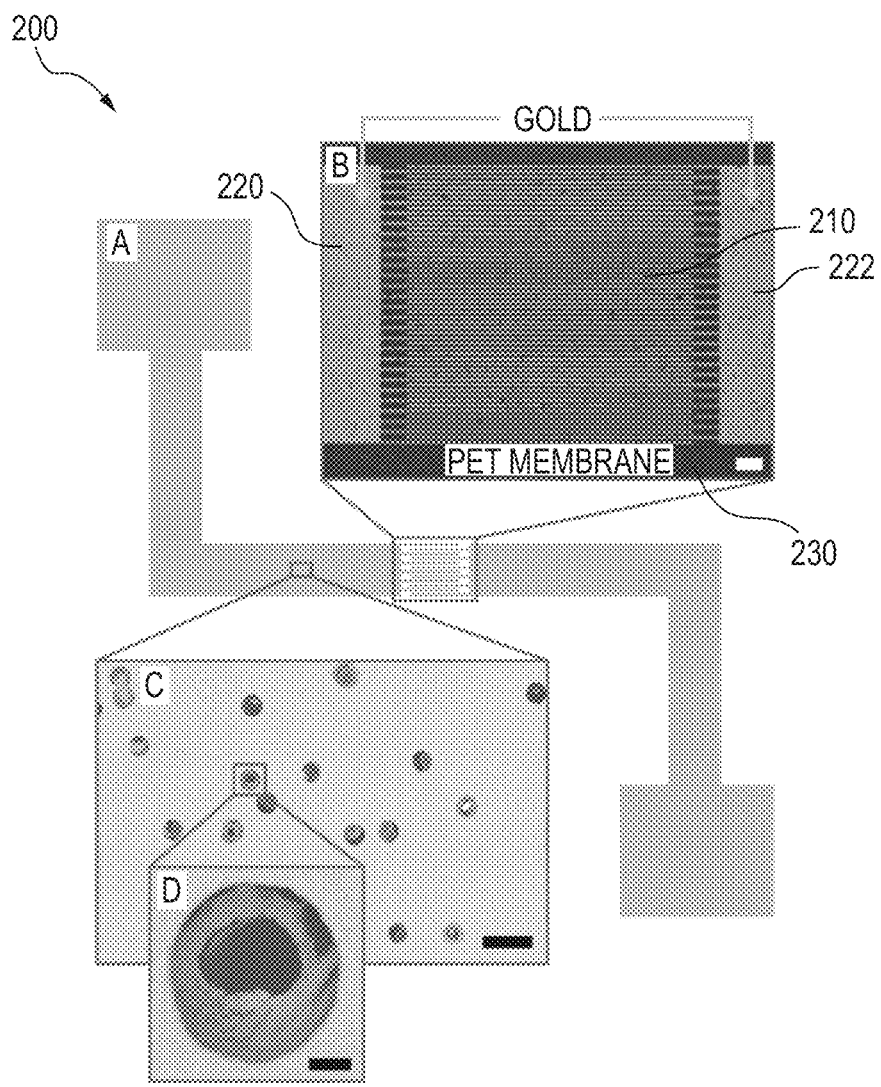
FIG. 9 is a schematic illustration of a microfluidic device and several regions detailed, in accordance with the present subject matter.

Specifically, the present subject matter provides the fabrication of gold microelectrodes on a permeable PET membrane. The resulting DEP microelectrodes were characterized by several techniques. In FIG. 9, a microfluidic system 200 in accordance with the present subject matter is shown. The system 200 comprises a plurality of gold electrodes 210. The interdigitated microelectrodes 210 shown in the center are linked to contact pads 220 and 222. FIG. 9, and specifically area B, shows an actual gold/PET surface. The continuous connection of the patterned gold is visible. The system 200 also comprises a PET membrane 230 upon which are disposed the electrodes 210 and pads 220, 222. The pores of the PET membrane 230 appear as black spots in the coated as well as uncoated areas of the surface. SEM images show the surface (area C in FIG. 9), and the insert (area D in FIG. 9). The extent of gold deposition, i.e. with regard to coverage or blockage of the micropores of the PET membrane, is best illustrated in area D of FIG. 9. SEM imaging showed dark grey spots inside the pores, i.e., the gold did not completely block them. The average distance to which the gold was deposited inside the pores was 2.1 µm±1.2 µm. These observations suggest that the pores remained open and therefore permeable. Even if the partial blockage would slightly affect the function of the membrane where gold was deposited, half of the cell adhesion surface area is not covered by it. Therefore, the permeability of the membrane remained effectively unaffected.

Specifically, FIG. 9 illustrates a scheme of the gold pattern and images of the gold patterned membrane. Area A shows a typical layout or configuration of the microfluidic system 200 having the microelectrodes in the center, which are connected to contact pads. Area B is a micrograph of the processed microelectrodes. Area C is an SEM image of the area used to measure the distance to which gold was deposited into the pores. The pores could be observed throughout the entire membrane. Area D is a detailed view of one pore showing its partial blockage by the deposited gold. The scale bar in area B is 100 µm, the scale bar in area C is 3 µm, and the scale bar in area D is 300 nm.

Figure 10A:
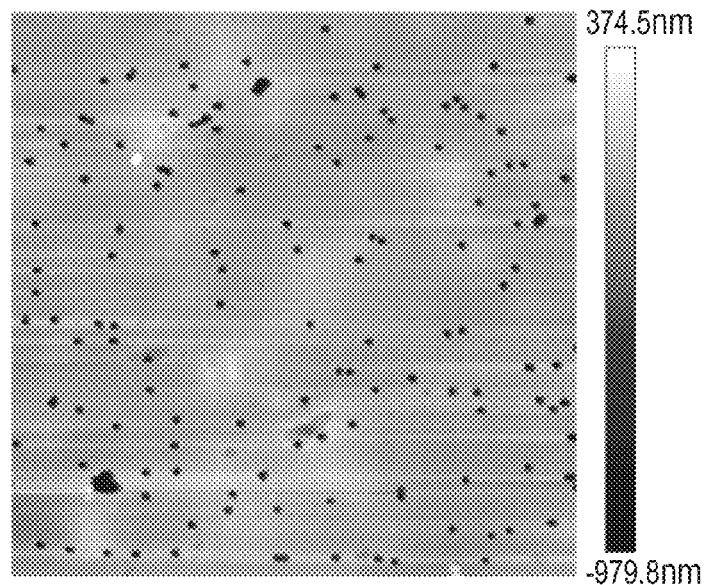
FIG. 10A is an image of a PET membrane before processing.
Figure 10B:
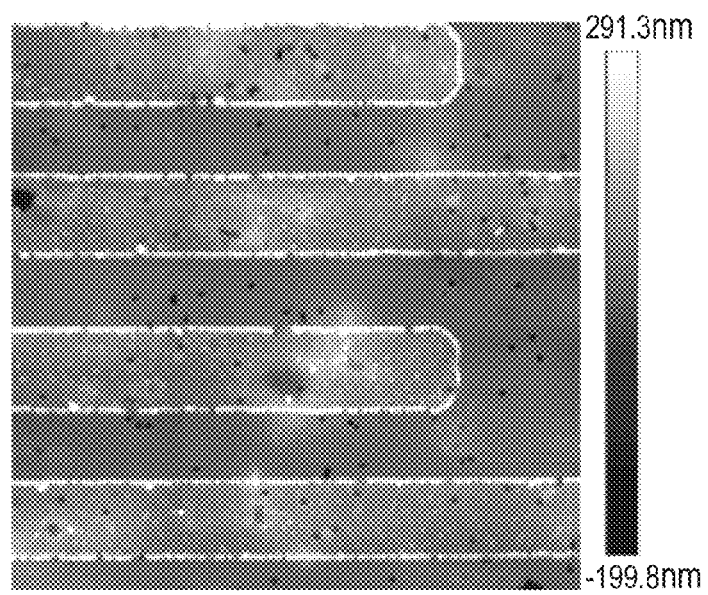
FIG. 10B is an image of a PET membrane after processing.

FIG. 10A and FIG. 10B are AFM micrographs of a PET membrane before (FIG. 10A) and after processing (FIG. 10B) in accordance with the present subject matter. The pores could be observed throughout the membrane regardless of the patterned gold. The coated areas within the pattern were continuously connected to result in interdigitated microelectrodes. In addition, the surface roughness of the PET membrane was measured before and after treatment to assess any possible changes during processing. An RMS (root-mean-square) roughness of 28.7 nm±4.8 nm was observed for the membrane before processing, and an RMS roughness of 24.3 nm±10.6 nm was observed after treatment. When these results were analyzed they showed no statistical difference (ANOVA, analysis of variance, single factor, p=0.33). Even the RMS roughness on the gold pattern (27.1 nm±9.6 nm) was not statistically different from the before and after processing values mentioned above (p=0.70 and p=0.61, respectively). The mechanical stability of the membrane was visually evaluated after processing, whereby no changes were detected. Both figures show a surface area of 75 μm×75 μm. The pores are randomly distributed and have an average diameter of 1.2 μm. The pores can be easily observed throughout the PET membrane including where the continuous layer of gold had been deposited.

As described in Example 3 herein, contact angle measurements were used to monitor the hydrophilicity of the membrane during the processing steps (see Table 1 later herein). With a water contact angle of 86° the membrane was slightly hydrophilic before any treatment. The sequential microfabrication steps decreased the contact angle to 69°, whereby the biggest change occurred after fixing the PET membrane onto the glass wafer via PMMA.

A multilayer microfluidic device 300 (see FIGS. 15 and 16) was assembled to test the permeability of the PET membrane after processing. The multilayer microfluidic device 300 comprises a glass substrate 310. A body 320 formed from a suitable polymeric material such as polydimethyl siloxane (PDMS) is disposed on the substrate 310. The body 320 defines at least two flow channels such as a bottom channel 330 and a top channel 350. The device 300 additionally comprises a PET membrane 340 disposed between and generally separating the flow channels 330 and 350. Two different food dyes were exchanged between the two layers by transporting them through the pores of the membrane (see FIGS. 11A-11D). This ultimately confirmed that its permeability was restored. Details as to this investigation are provided in the description of Example 2 herein.

Specifically, FIGS. 11A-11D illustrate permeability testing of the PET membrane after processing. FIGS. 11A-11D show actual images of light and dark food dyes exchanged between the channels 330, 350 in the multilayer microfluidic device 300 by their transport through the pores of the PET membrane 340. Two flow channels 330, 350 were provided for the dyes. The light dye flowed from left to right and the dark dye from top to bottom. The lower regions of FIGS. 11A-11D show the corresponding flow patterns of the food dyes in the channels 330, 350. In FIG. 11A, at t=0 both flow rates were 0.5 μl/min, resulting in a mixture at the intersection at membrane 340. In FIG. 11B, after changing the flow rates (light: 10 μl/min, dark: 0 μl/min) the light dye was transported to the top channel 350 through the membrane 340 and filled the top channel 350 (approximately t=3 min). In FIG. 11C, after inverting the flow rates the dark dye was transported to the bottom channel 330 and filled the channel (approximately t=7 min). And in FIG. 11D, a combined mixture occurred after setting both flow rates back to 0.5 μl/min (approximately t=11 min). The scale bars in FIGS. 11A-11D are 100 μm.

Figure 12:
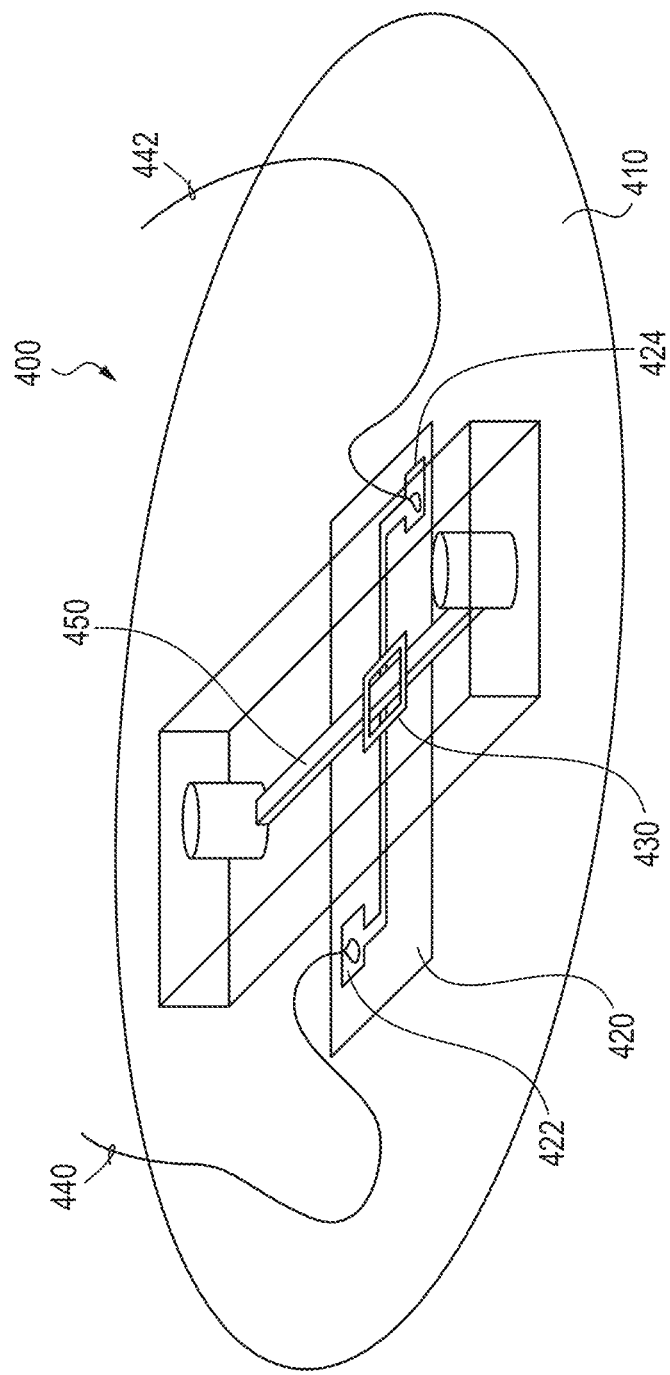
FIG. 12 is a schematic illustration of another microfluidic device in accordance with the present subject matter.

The microelectrodes were evaluated for dielectrophoretic cell capture. In order to do this, a microfluidic device was assembled by placing a poly(dimethyl siloxane) (PDMS) microfluidic channel perpendicular to the microelectrodes. Specifically, referring to FIG. 12, a schematic illustration of the assembled microfluidic device is shown. A piece of PET membrane with deposited gold electrodes was fixed onto a glass wafer. The location of the microelectrodes is indicated by the square at the 430. The PDMS microfluidic channel was assembled on top, perpendicular to the microelectrodes. Wires were glued to the contact pads and connected to a waveform generator. Specifically, the microfluidic device 400 comprises a glass substrate 410, an assembly 420 of a PET membrane with electrically conductive electrodes, and at least one microfluidic channel 450 disposed on the assembly 420 of the membrane and electrodes. The assembly 420 includes contacts such as 422 and 424, at which a voltage source is connected such as through wires or other electrical conductors 440, 442.

For the cell trapping experiment NIH-3T3 cells were harvested in low-conductive media (to perform positive DEP) and inserted into the microchannel, prefilled with the same media. To avoid cell damage the dielectrophoretic cell capture was carried out within 5 minutes after harvesting the cells. Trapped cells were collected in about half of the microelectrode surfaces by varying the applied voltage from 2 $V_{p-p}$ to 5 $V_{p-p}$ at a frequency of 10 MHz. Variations in the voltage allowed for cell capture across the length of the microelectrode array. When cells experienced higher electric fields they were trapped on the first few electrodes. On the other hand, when lower electric fields were applied cells tended to be trapped further down on the microelectrode array. The trapping efficiency could be increased further by either using a highly concentrated cell suspension or longer periods of DEP trapping. Additionally, the cell trapping efficiency can be influenced by the design of the microelectrodes. By modifying the configuration of the electrodes this could be further improved. Most of the trapped cells (approximately 90%) still remained on the PEMs after switching off the DEP forces and exchanging the low-conductive media with cell culture media. Cells attached well, as observed in FIG. 13A. A live/dead assay was carried out 24 hours after cell attachment. The assay showed that about 99% of the cells emitted green fluorescence; i.e., these cells were alive, see FIG. 13B.

Figure 13B:
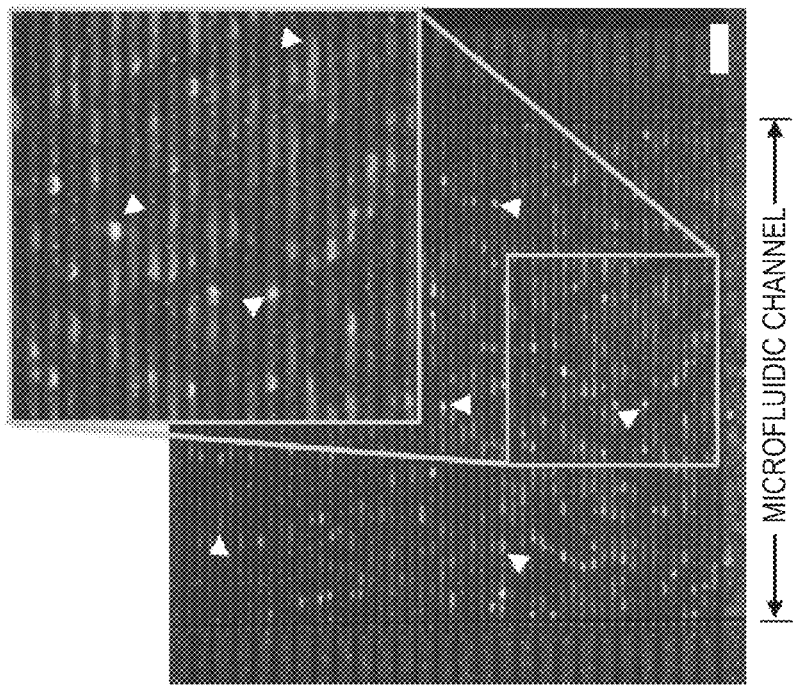
FIG. 13B is an image of the trapped cells on the microelectrode surface 24 hours after trapping.
Figure 13A:
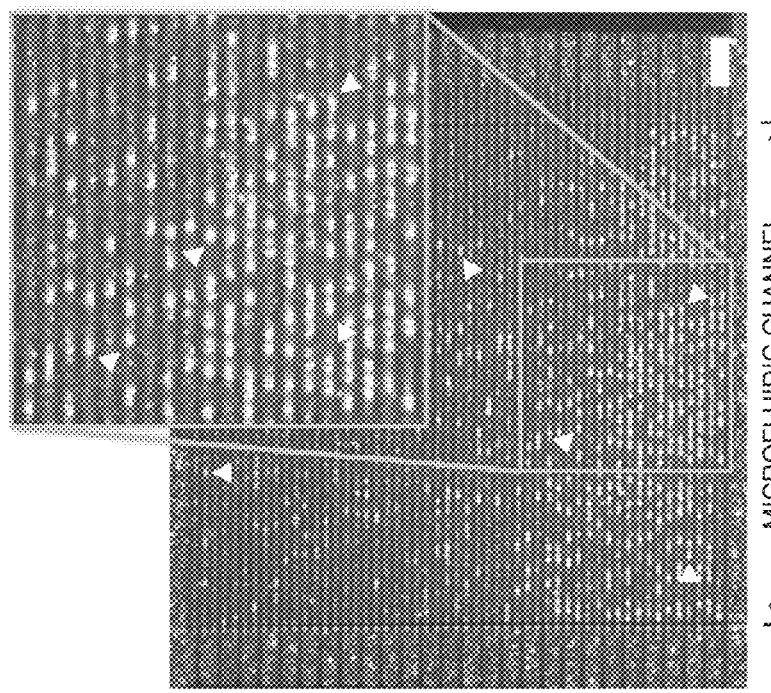
FIG. 13A is an image of a collection of trapped cells on a micro electrode surface in a flow channel.

Specifically, FIGS. 13A and 13B show efficient cell capture using DEP. FIG. 13A is a micrograph after switching off DEP forces and exchanging low-conductive media with cell culture media (0 h). NIH-3T3 cell capture was evident, as soon as 5 minutes from the time the microelectrodes were energized. Cells flowed from bottom to top of the figure during DEP trapping. Arrowheads point at some of the trapped cells. FIG. 13B shows a live/dead staining 24 hours after cell capture was carried out. The cells spread onto the membrane and green fluorescence could be observed in approximately 99% of the cells, demonstrating that cells were viable. The arrowheads in FIG. 13B point to some of the viable cells. Inserts show some of the trapped cells in more detail. The scale bars in FIGS. 13A and 13B are 100 μm.

Figure 14:
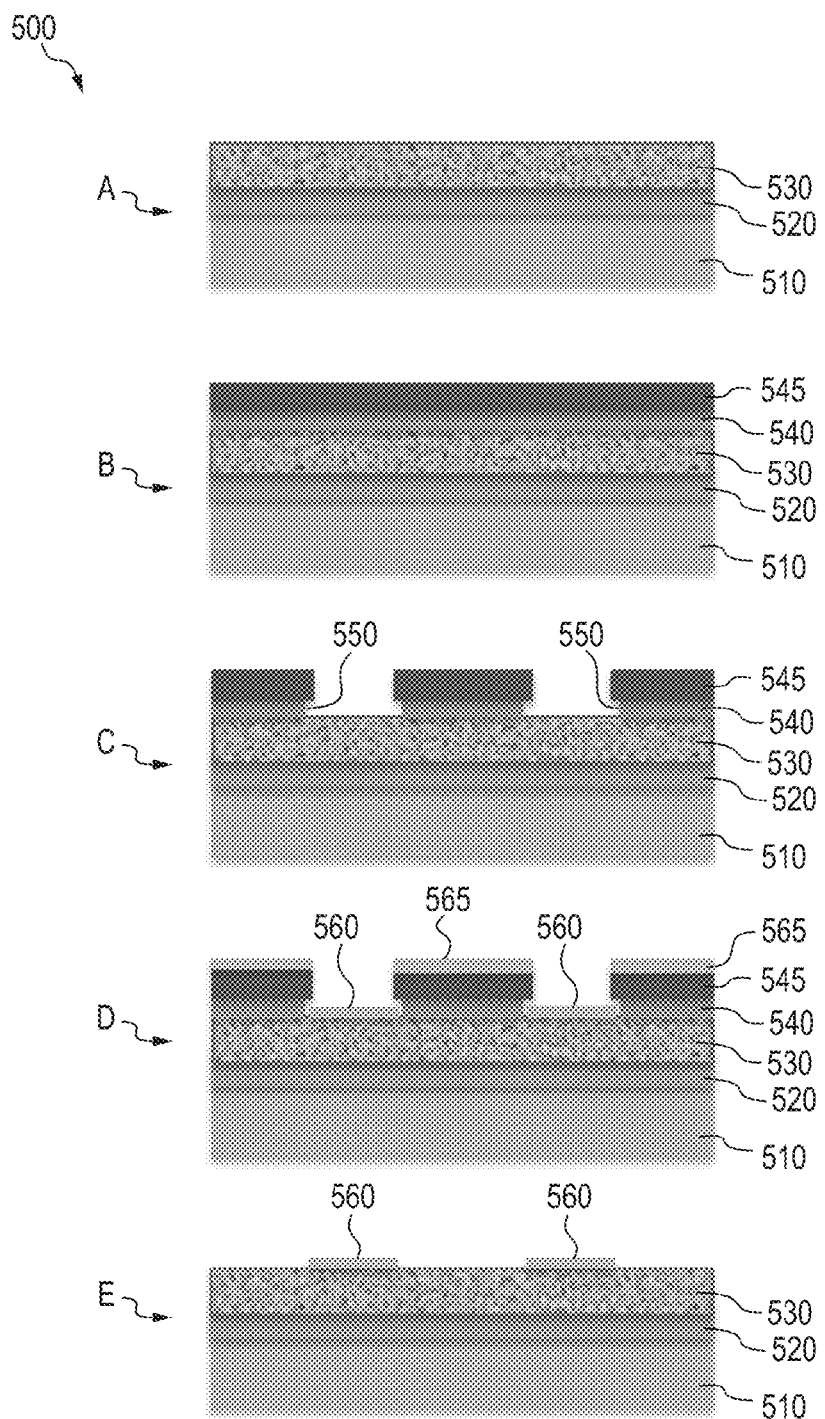
FIG. 14 is a collection of images illustrating a method of forming electrically conductive regions on a PET membrane in accordance with the present subject matter.

FIG. 14 illustrates a method 500 of forming a plurality of gold electrodes on a PET membrane in accordance with the present subject matter. In stage A, a layer 520 of an adhesive such as PMMA is deposited onto a suitable substrate such as a glass wafer 510. Deposition of the adhesive can be performed by a wide array of techniques, such as spin coating. A polyester, e.g. PET, membrane 530 is applied onto a face of the adhesive layer 520. In stage B, two layers 540 and 545 of photoresist material(s) are applied such as by spin coating onto the PET membrane 530. In stage C, the photoresist face of the intermediate assembly from stage B is exposed to UV light to form stepped undercuts 550 between the two layers 540, 545 of the photoresist materials. In stage D, thin layered regions 560, 565 of gold are deposited on the exposed upwardly directed surfaces of the intermediate assembly from stage C. Specifically, a collection of lower gold regions 560 and a collection of upper gold regions 565 form. It will be noted that a continuous layer of gold does not form between the lower and upper gold regions 560, 565 due to the stepped undercuts 550. In stage E, the photoresist bilayer, i.e. layers 540 and 545, and the upper gold regions 565 are removed to thereby leave the lower gold regions 560 on the PET membrane 530. Additional details related to the method 500, materials, and intermediate and resulting structure are provided in the description of Example 2 herein.

Figure 17:
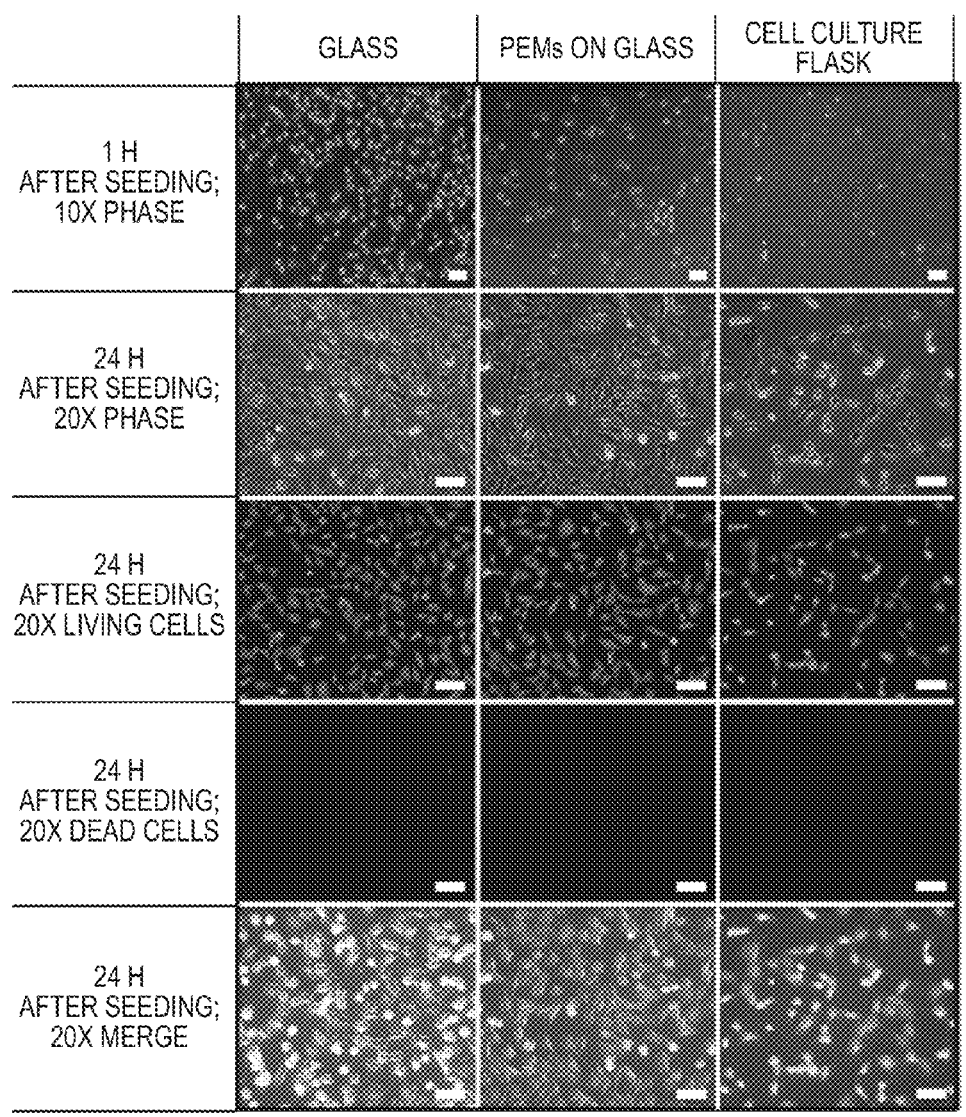
FIG. 17 is a collection of images showing cell behavior on an array of different surfaces.

FIG. 17 is a collection of images illustrating cell behavior at various stages and on different surfaces. The details of this investigation are provided in the description of Example 3 herein.

DEP has been widely used in microfluidic platforms. The choice of platform will depend on the evaluations to be carried out. The type of bioparticle (e.g., cells and viruses) to be manipulated defines guidelines such as the design of the electrodes or performing experiments with or without flow. For example, hematopoietic tumor cells were analyzed using a DEP system without applied flow. The electrodes generated cell trapping forces and at the same time created electrothermal vortices that produced efficient drug mixing, allowing for the analysis of cancer drug-induced cytotoxicity. A similar experiment was carried out where hepatitis A viruses were trapped in a microsystem using electro-hydrodynamic flow and DEP forces. These kinds of systems use non-adherent bioparticles and therefore provide platforms that can usually be reused several times. However, studies using adherent cells mostly require cell adhesive molecules on top of the electrodes to allow cell behavior and, hence, cell responses that would provide meaningful data. Since cells tend to rearrange the adhesive molecules they attach onto and leave behind residues from their own extracellular matrix after detaching, the number of times the devices can be reused is limited. When cells are used in a microfluidic platform it is beneficial to have some form of trapping mechanism. However, the use of, for example, mechanical traps creates areas with different flow velocities, hence influencing the flow near the cells. This could likely affect the results of experiments in the cases where cells are sensitive to such shear forces. In contrast, DEP systems with planar electrodes render a channel without features that disturb the flow.

The results demonstrate the functionality of the patterned microelectrodes on the permeable PET membrane for dielectrophoretic cell capture. This membrane along with DEP would be suited for specialized applications such as studies of drug transport, cell monolayer permeability and cell co-cultures, among others. However, these applications would gain the most when combined with multilayer microfluidic devices. The added levels of control and the benefit of the localized cell enrichment by DEP trapping are at the heart of these devices. In addition, the combination of DEP and PEMs on a permeable PET membrane allows fast and reliable cell capture at a high efficiency, and hence subsequent long term cell culture is achievable.

The present subject matter provides the use of gold or other electrically conductive microelectrodes on PET membranes as substrates to perform DEP cell entrapment in a microfluidic device. The microelectrodes for DEP were fabricated using conventional photolithographic and metallization processes. The membrane was characterized with different techniques, and results showed that there was no difference in terms of hydrophilicity, roughness, and permeability of the membrane when comparing the before and after processing surfaces. Finally, it was demonstrated that the patterned electrodes can be used for DEP cell trapping experiments in a microfluidic channel. The cell viability assessment showed that cells were viable 24 hours after DEP trapping, demonstrating that long term cell experiments can be carried out. This approach allows for an easy and rapid way of cell entrapment and enrichment onto PET membrane surfaces. By combining this work with multilayer microfluidic devices a new platform for cell-cell interactions or cell co-culture studies could be developed. Cell exposure to different microenvironments would be possible, having two cell types physically separated. Future work will focus on the use of these membranes in multilayered microfluidic systems for cell-cell interaction studies.

EXAMPLES

Materials

Example 1

Poly(allylamine hydrochloride) (PAH, MW=70,000), PAH-Fluorescein isothiocyanate (FITC), monoclonal anti-neurofilament antibody produced in mouse, antimouse IgG-FITC, retinoic acid 98%, FN, sucrose, poly-L-lysine, and polystyrene pellets were purchased from Sigma-Aldrich (St. Louis, Mo.). Poly(styrenesulfonic acid) (PSS, MW=70,000) was purchased from Polysciences, Inc. (Warrington, Pa.). Poly(dimethylsiloxane) (PDMS, Sylgard 184) was purchased from Dow Corning (Midland, Mich.). Alpha Minimum Essential Medium (αMEM) with ribonucleosides and deoxyribonucleosides, calcein AM, ethidium homodimer-1,6-carboxy-X-rhodamine, succinimidyl ester (6-ROX-NHS), and fetal bovine serum (FBS) were obtained from Invitrogen Corporation (Carlsbad, Calif.). P19 cells, 0.25% trypsin-ethylenediaminetetraacetic acid (EDTA) and calf bovine serum (CBS) were purchased from ATCC (Manassas, Va.). Purecol (acidified bovine collagen I) was purchased from Advanced BioMatrix (San Diego, Calif.). Dulbecco's phosphate-buffered saline (DPBS) and phosphate-buffered saline (PBS) were obtained from Mediatech, Inc. (Hernon, Va.). Indium tin oxide (ITO)/glass substrates were purchased from Delta Technologies (Stillwater, Minn.), and 22 mm×22 mm #1.5 Corning coverslips were obtained from Daigger (Vernon Hills, Ill.). Electrically conductive adhesive was purchased from Epoxy Technology Inc. (Billerica, Mass.). Octyldimethylchlorosilane was obtained from Gelest (Morrisville, Pa.). SU-8 photoresist and developer were obtained from MicroChem Corp. (Newton, Mass.).

Cell Culture

P19 cells were cultured in αMEM with ribonucleosides and deoxyribonucleosides. The growth medium was supplemented by adding 7.5% of bovine calf serum and 2.5% fetal bovine serum (37.5 mL and 12.5 mL in a total of 500 mL of αMEM, respectively). Growth medium was renewed every 2 d, and cells were subcultured every 2 days to 3 days at a dilution ratio of 1:10. Cells were maintained in a humidified environment with 5% carbon dioxide and a temperature of 37° C.

Coverslips were cleaned with isopropyl alcohol (IPA) using a lint-free cloth wipe and were blown dry with compressed nitrogen ($N_2$) before placing them flat on a glass Petri dish. An 8 mg/mL polystyrene (PS) solution prepared in toluene was spin coated (418.9 rad/s, 50 s) onto the coverslips, and the PS-spin coated coverslips (PS thickness between 55 nm to 85 nm) were placed in a vacuum chamber for 3 hours to remove any residual solvent. All PS-coated coverslips were plasma oxidized prior to cell adhesive material deposition.

Cells were seeded in sucrose and in cell culture media (CCM) on coverslips coated with natural or synthetic materials. Incubation times were different for each material and pretreatment. Coverslips pretreated with CCM prior to cell seeding were incubated with the CCM for 1 hour at 37° C. Additional coverslips were incubated with Collagen I (Col I, 30 µg/mL), poly-L-Lysine (1 mg/mL), and FN (25 µg/mL to 50 µg/mL) for 90 minutes at 4° C. PAH and PSS solutions (1 mg/mL, mol/L (M) concentrations of the repeating units: PAH=10.7 mmol $L^{-1}$ and PSS=4.8 mmol $L^{-1}$) were each prepared in 18.2 MO filtered deionized water (DI-water). The pH of the PAH and PSS solutions was adjusted to 5 and 6, respectively. Four alternating PEMs, $(PAH/PSS)_2$, were deposited onto the oxidized PS surface of the coverslips by immersing the coverslip in the polyelectrolyte solutions sequentially. The initial PAH layer was deposited for 40 min. The coverslip surface was rinsed with DI-water twice before applying subsequent alternating layers for 10 minutes with two DI-water rinses between each incubation. After the fourth layer was deposited, the PAH outermost layer (fifth layer) was deposited for at least 30 minutes at room temperature (approximately 21° C.±2° C.). P19 cells were then seeded in a 0.32 mol/L sucrose solution for 15 minutes at room temperature, and then the sucrose was aspirated and CCM was added to the cells. Images at 0 hours (after adding CCM at the end of sucrose exposure) and 24 hours were taken to assess the morphology differences and adherent status of the seeded cells. The number of cells adhered to the substrates and the number of rounded (i.e. unhealthy) cells were determined with ImageJ software and the surface that had the highest number of cells with the lowest number of rounded cells were selected for use in the DEP device.

Coverslips for the deposition of the hCAM were prepared using the same procedure previously described, but to promote better adhesion of the spin-coated polystyrene the following silanization step was added prior to spin coating the polystyrene. Cleaned coverslips in a Petri dish were placed in a dessicating chamber containing a Teflon holder with 200 µL of octyldimethylchlorosilane. House vacuum was applied to the chamber for 2 h, and then the Petri dish was placed in a 60° C. oven for at least 3 h. All PS-coated coverslips were plasma oxidized prior to PEM deposition. PEMs were deposited as described in the previous section, except that after the fourth layer was deposited, the wells were rinsed twice and then stored overnight with DI water at room temperature.

The PEM coated coverslips were then incubated in a 50 µg/mL solution of FN prepared in DPBS at 4° C. for 1.5 h. The coverslips were rinsed twice with PBS, and the final hCAM layer was deposited by incubating the coverslips in 1 mg/mL PAH for 45 minutes at 4° C. The hCAM coverslips were rinsed twice with DI-water and then transferred to PBS in a new well in a 6-well cell culture plate until cell seeding.

The hCAM was deposited on the ITO electrode substrates as described above, except it was applied in a microfluidic polydimethylsiloxane (PDMS) channel covering the DEP electrodes. In this case, the solutions were added to the channel inlet and flowed down the channel previously aligned onto the DEP electrodes. Once each deposition was completed, the solutions were aspirated via the channel outlet. The incubation times and the concentration of the solutions remained the same.

A 0.32 mol/L (M) sucrose solution was prepared in DI-water to mimic the osmolarity of the P19 cell culture media but with low electrolyte concentration to maximize DEP forces. Confluent (80%) P19 cells were trypsinized with 0.25% trypsin-EDTA, and were divided into two 15 mL centrifuge tubes. The cells were centrifuged for 7 minutes at 83.8 rad/s and 5° C. At this point the cells were ready for incubation with sucrose at different time points (0 min, 15 min, 30 min, 45 min, 60 min). For the 0 minutes sample, one tube of cells was resuspended in cell culture media, and the cells were seeded onto the hCAM coverslips at a dilution ratio of 1:10 (approximately 4700 cells/$cm^2$). The second tube of cells was resuspended in the sucrose solution, and the cells were seeded onto the same substrate at an identical cell seeding density (approximately 4700 cells/$cm^2$). After each sucrose incubation time point, 4 mL of cell growth media was added to the samples to dilute the sucrose (a 1/27 dilution, 3.7 final sucrose solution) and restore to normal cell culture conditions. Phase contrast images of the P19 cell growth on the hCAM were taken at 0 h, 24 h, and 48 h.

P19 cell viability on the hCAM surface was assessed after 48 hours using the LIVE/DEAD viability assay kit from Invitrogen Corp. Calcein AM (excitation/emission maxima at 495 nm/515 nm) was used to stain the viable cells, which exhibit intracellular esterase activity, while ethidium homodimer-1 (EthD-1) (excitation/emission maxima at 495 nm/635 nm) was used to label dead cells with damaged plasma membranes.

Calcein AM and EthD-1 were diluted to 2 µmol/L and 4 µmol/L, respectively, in a single solution in DPBS. 1 mL of the dye solution was added to each well, and the 6-well plates were placed in the incubator for 45 min. The cells were imaged immediately using phase contrast optics and FITC and Rhodamine filter sets. The images were taken in triplicates for each time point. Viable and dead cells were counted manually, and the percentage of each was expressed based on the total number of cells per frame. A minimum of 440 cells, per frame, were counted.

SU-8 masters with raised features (30 µm to 35 µm height, 1000 µm wide) for molding PDMS microchannels were fabricated using the manufacturer's protocol. PDMS microfluidic structures were molded by pouring the polymer on the SU-8 master and curing at 100° C. for 1 hour (from manufacturer's product information sheet).

ITO electrodes were made from ITO/glass substrates. The ITO surface was patterned using conventional photolithographic methods. A negative photoresist was spin coated on the ITO surface and then exposed to UV light through a chrome mask containing the electrode design. The pattern was developed, and the exposed ITO was etched using a 9 mol/L (M) hydrochloric acid (HCl) solution. The remaining ITO pattern was then exposed by dissolving the remaining photoresist on the substrate. Wire connections were made by bonding silver/copper wires to ITO pads using an electrically conductive adhesive (H37-MPT, Epoxy Technology, Inc.) heated at 150° C. for 1 hour (from manufacturer's product data sheet).

P19 cells were detached from the cell culture surface by trypsinization, centrifuged at 83.8 rad/s for 7 minutes at 5° C., and then resuspended in 0.32 mol/L sucrose. The cells were immediately introduced into the microfluidic channel covering the electrodes via the inlet reservoir. Approximately 150 µL of the cells resuspended (approximately 375,000 cells) in sucrose were added to the inlet that accessed the channel previously filled with the sucrose solution. A flow was produced when the cells were introduced due to the difference in pressure between the inlet and outlet reservoirs. Once the cells started to flow down the channel, a sine wave of up to 7 $V_{p\text{-}p}$ was applied at a frequency of 30 MHz. The cells were exposed to the DEP forces for up to 4 minutes at which point the DEP electrodes were de-energized. Then, the cells/sucrose solution in the inlet reservoir was exchanged for cell culture media to replace the sucrose in the channel. The DEP device with the trapped cells in cell culture media was then placed in the incubator set at 37° C. and 5% $CO_2$.

The cells were maintained by adding fresh cell culture media to the inlet reservoir every 24 h, and by removing the media collected in the outlet or waste reservoir at the same time. Images of the cells were taken every 24 h.

P19 cells are typically induced in suspension. However, the present approach requires the induction procedure to be carried out on a surface (hCAM) rather than in suspension. Therefore, P19 cells were first induced on tissue culture polystyrene (TCPS) to determine if it was feasible to induce them on a surface, and then the cells were induced on (PAH/PSS)$_2$/FN and hCAM. The results on the three surfaces were then compared. Induction on all surfaces was carried out using the same conditions in terms of chemicals and days of induction. The only difference was the surface onto which the P19 cells were attached. The procedure that follows applied to all inductions. To induce the differentiation of P19 cells, the CCM was replaced by induction media (IM) comprised of αMEM supplemented with 5% FBS and retinoic acid at a final concentration of 0.5 μmol/L. IM was changed every 24 hours for a period of 4 days. On day 4, the IM was replaced with CCM, which in turn was replaced every 24 hours for two days. Cell differentiation was verified by using a fluorescently labeled antibody to stain for marker proteins associated with neuronal differentiation two days after cell induction was completed.

Differentiated P19 cells were fixed by first rinsing the cells with PBS and then adding 4% paraformaldehyde in PBS. The fixation was allowed to occur at room temperature for 10 minutes at which time the cells were rinsed with PBS. Cells were then permeabilized with a solution of 0.25% Triton X-100 in PBS and then incubated with the primary antibody (monoclonal antineurofilament) at a dilution of 1:40 for 3 hours at room temperature. The samples were rinsed with PBS and incubated at room temperature with a secondary antibody (antimouse IgG-FITC, Cat. No. F9137, Sigma-Aldrich) at a dilution of 1:200 for up to 90 min. The neurofilament staining was observed with a 200M Zeiss microscope using a mercury lamp source and a filter set with a band pass for excitation at 450 nm to 490 nm, a dichroic beam splitter at 510 nm, and a band pass for emission at 515 nm to 565 nm. The objective used had a 10× magnification and an aperture of 0.3. Images were taken using a Zeiss MRm camera.

Example 2

Fabrication of gold electrodes on a PET membrane is shown in FIG. 14. The PET membrane was first fixed onto a glass wafer using poly(methyl methacrylate) (PMMA) as adhesive, to prevent folding. Gold microelectrodes were fabricated on top of the PET membrane using conventional photolithographic and metallization techniques. The resulting microelectrodes were characterized by AFM, SEM, and optical microscopy. Polyelectrolyte multilayers (PEMs) were deposited onto the surface of the PET membrane containing the microelectrodes in order to trap and anchor cells. Subsequently, the microfluidic device was assembled and the microelectrodes were tested for cell capture by applying DEP forces. Cell viability was assessed 24 hours after cell capture.

Fixation of the PET membrane (11 μm thick, 1.2 μm pore size, $1.6 \times 10^6$ pores per $cm^2$, cell culture treated, it4ip, Belgium) was necessary for photolithographic processing to prevent folding of the membrane and hence to avoid problems with the gold patterning. Therefore, 495 PMMA A 11 (MicroChem, Newton, Mass.) was spin coated onto a 4 inch (10.16 cm) glass wafer (Valley Design Corp., Shirley, Mass.) to a thickness of 2.25 μm. A piece of PET membrane of about 2 cm×2 cm was placed in the middle of the wafer, and then the wafer was baked at 110° C. for 5 min. For the bilayer lift-off process two different photoresists were spin coated onto the membrane. First, the membrane was coated with the lift-off resist LOR 3A (MicroChem, Newton, Mass.) to a thickness of 350 nm and baked at 155° C. for 10 min. Second, the positive tone photoresist S1813 (Rohm & Haas, Marlborough, Mass.) was spun to a thickness of 1.2 μm and baked at 110° C. for 5 min. Next, the wafer was exposed to UV-light ($\lambda=405$ nm) for 5 seconds (MA/BA6, SUSS MicroTec AG, Garching, Germany) to transfer the pattern of the microelectrodes (1000 μm long and 10 μm wide with gaps between opposite electrodes of 10 μm) onto the photoresist. Finally, the pattern was developed in MF-319 (Rohm & Haas, Marlborough, Mass.) for 60 s. Afterwards, the wafer was placed overnight under vacuum to allow complete drying of the membrane.

A 50 nm thick layer of gold was deposited onto the photolithographically processed wafer (E-bream evaporator Denton Infinity 22, Denton Vacuum LLC, Moorestown, N.J.). Redundant gold was lifted-off in 1165 remover (MicroChem, Newton, Mass.). To support and accelerate the process, agitation and short pulses of sonication (3 seconds to 5 seconds) were applied. The lift-off was completed within 5 minutes to 10 minutes. After the lift-off process the sample was blow dried. The dimensions of the microelectrodes after all processing steps varied slightly from the design pattern (electrodes widths of approximately 11 μm and gaps of approximately 9 μm).

The distance to which gold was deposited into the pores was assessed by imaging a total of 10 pores, randomly selected, with field-emission SEM (Ultra-60 FESEM, Zeiss, Germany). To obtain the distance to which gold was deposited into the pores, the difference in the working distances of two SEM images in the same pore were measured: the first image was focused on the surface of the membrane (as outer value), and the second one was focused on the deepest point inside the pore where gold was still seen (as inner value). The difference between the inner and outer working distances corresponded to the distance to which the gold was deposited inside the pore.

AFM images (Dimension 5000, Digital Instruments, Santa Barbara, Calif.) were acquired in tapping mode. Images were acquired at ambient conditions on dry samples. To obtain the differences in RMS roughness of the surfaces within the samples, seven independent areas of 10 μm×10 μm were imaged and then analyzed using the Nanoscope 7.3 software. The analyzed surfaces were: 1) membrane before processing; 2) membrane after processing; and 3) the gold patterned.

Contact angles were measured to characterize the hydrophilicity of the PET membrane during the processing. A drop of water was placed onto the sample, and a side view picture was taken. The droplet curvature was fitted using the software FTA32 (First Ten Angstroms, Inc., Portsmouth, Va.) to obtain the contact angle value. A contact angle between 0° and 90° was defined as a hydrophilic surface and a value between 90° and 180° as a hydrophobic surface. For each step during the electrode microfabrication the contact angle was averaged from four independent measurements.

The SU-8 master (SU-8 2025, MicroChem, Newton, Mass.) contained features for molding a microchannel out of PMDS (Sylgard 184, Dow Corning, Midland, Mich.) with a height of 30 μm and a width of 1000 μm. It was fabricated using the manufacturer's protocol. PDMS was cured on the SU-8 master after mixing the elastomer and curing agent at a ratio of 10:1, respectively. Once mixed and degassed, the mixture was poured onto the SU-8 wafer and cured for 4 hours at 65° C. Excessive PDMS was cut, and access holes of approximately 5 mm were punched. The PDMS microchannel was rinsed with 70% ethanol before it was assembled onto the substrate.

Figure 15:
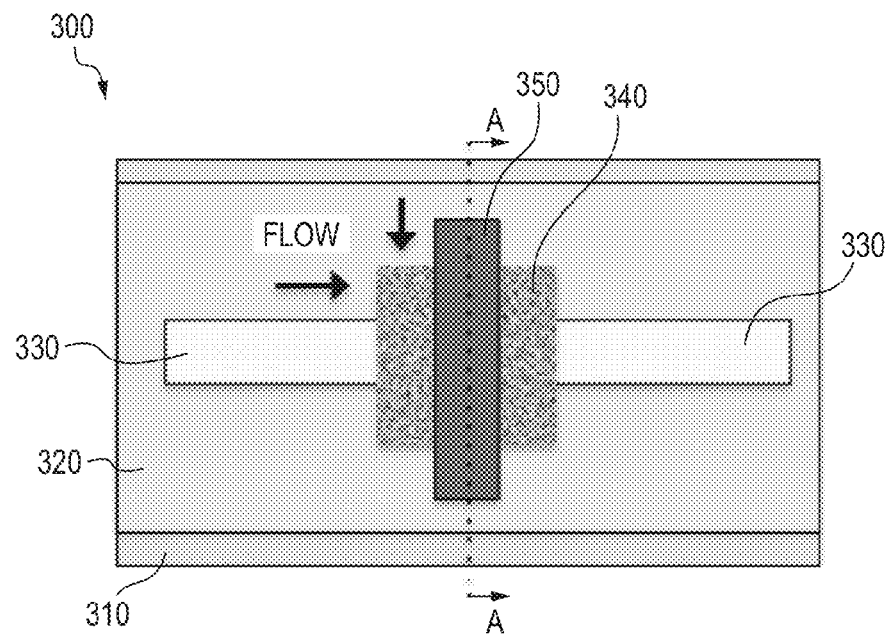
FIG. 15 is a schematic top view of a microfluidic device including a PET membrane in accordance with the present subject matter.
Figure 16:
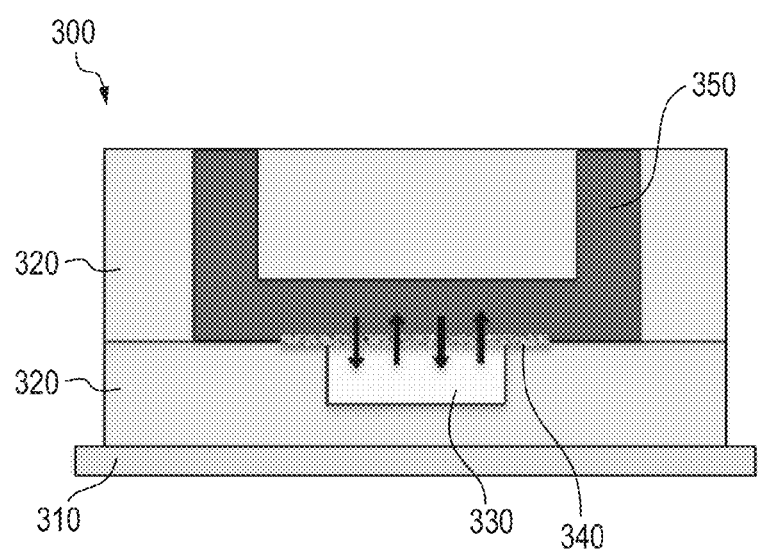
FIG. 16 is a schematic cross sectional view of the device in FIG. 15 taken across line A-A.

A multilayer microfluidic device as shown in FIGS. 15 and 16, was assembled to confirm that the permeability of the PET membrane was not affected during processing. The membrane was transferred onto a PDMS layer containing the top channel. Next, the PMMA was dissolved in acetone. The PDMS layer containing the membrane was plasma activated along with the PDMS layer containing the bottom channel. The membrane was sandwiched between both PDMS layers to complete the assembly of the device. Both layers contained a microfluidic channel of 30 μm in height and 1000 μm in width. These channels were perpendicularly aligned to each other, whereby the intermediate PET membrane allowed the exchange of reagents. Tubing was connected between the assembled microchip and syringe pumps (PHD 2000, Harvard Apparatus, Pa.). For the permeability test the flow rates varied between 0, 0.5 and 10 μl/min. Specifically, referring to FIGS. 15 and 16, the processed PET membrane was aligned between the channels of the top and bottom PDMS layers. FIG. 15 indicates the flow directions in both channels. The assembled device is comprised of a glass substrate, the bottom PDMS layer, the membrane, and the top PDMS layer. The dashed line in the top view denotes the position at which the cross section of FIG. 16 is taken. The cross section indicates the area where the exchange of reagents between the channels was possible, only through the pores of the PET membrane (see arrows).

To enable cell anchorage and cell culture on chip after dielectrophoretic cell capture, the area of the membrane containing the microelectrodes was coated with PEMs as described in Reyes et al. Briefly, 5 μL of a 1 mg/mL poly (ethyleneimine) solution (Molecular Weight (MW)=70000, Polysciences, Inc., Warrington, Pa.) were placed on the microelectrodes. This first layer was incubated for 30 min, rinsed with water, and blow dried. Next, two bilayers of polyanion/polycation were deposited (polyanion=sodium poly(styrene sulfonate), MW=70000, Polysciences, Inc., Warrington, Pa.; and polycation=poly(allylamine hydrochloride), MW=70000, Sigma-Aldrich Corp., St. Louis, Mo.; 1 mg/mL each). Each layer was incubated for 10 min, rinsed with water, and blow dried. These procedures resulted in the deposition of a total of five layers of polyions on the microelectrodes.

NIH-3T3 mouse embryonic fibroblast cells were cultured in DMEM (Dulbecco's Modified Eagle's Medium) modified with 10% (v/v) bovine calf serum. Media was replaced every other day, and cells were subcultured when they were 80% confluent using 0.25% (w/v) trypsin (all reagents from ATCC, Manassas, Va.). For DEP experiments the cells were harvested in 0.147 mol/L sucrose (Sigma-Aldrich Corp., St. Louis, Mo.). Sucrose, a non-electrolyte, was used as low-conductive media to perform positive DEP, i.e., the cells were attracted by the DEP forces.

Wires were connected to the contact pads using an electrically conductive adhesive (Epoxy Technology Inc., Billerica, Mass.), cured for 1 hour at 150° C. Then, the membrane was coated with PEMs as previously described herein. Finally, the device was assembled by placing the cleaned PDMS microchannel on top of the microelectrodes, so that the channel was perpendicular to the microelectrodes. The assembled device was connected to a waveform generator (Agilent Technologies, Santa Clara, Calif.), and the channel was filled with 0.147 mol/L sucrose using capillary forces. 150 μL of the cell suspension were placed into the inlet of the microchannel. Suction was applied from the outlet to start the cell flow (linear velocity of approximately 550 μm/s). Cells were captured by applying a sine wave from 2 $V_{p-p}$ to 5 $V_{p-p}$ at a frequency of 10 MHz for less than 5 min. Subsequently, the cell/sucrose solution in the inlet was exchanged with cell culture media, and the device was placed in the incubator at 37° C. and 5% $CO_2$. After 24 hours a live/dead assay (Live/Dead® viability/cytotoxicity kit, Invitrogen, Eugene, Oreg.) was performed as described in the manufacture's protocol. Briefly, before imaging, the cells were incubated in media containing 2 μmol/L Calcein AM and 4 μmol/L Ethidium homodimer-1 for 20 min. Green fluorescence indicated living cells and red fluorescence dead ones.

Additionally, cell adhesion and viability of NIH-3T3 cells was tested directly on glass, on PEMs on glass and in a cell culture flask. Therefore, the cells were seeded onto these surfaces and incubated for 24 hours at 37° C. and 5% $CO_2$. Afterwards a live/dead assay was performed as described above.

Example 3

Water contact angles were measured at different points during the fabrication process to monitor changes in hydrophilicity of the PET membrane. The results of this evaluation are presented below in Table 1.

TABLE 1

Water contact angles of the PET membrane (n = 4).

| Point of Measurement | Contact Angle [°] |
|---|---|
| before processing | 86 ± 1 |
| on PMMA | 74 ± 1 |
| after development | 73 ± 1 |
| after lift-off | 69 ± 2 |

To compare the NIH-3T3 cell behavior on our PEMs/PET membrane with standard cell culture, cell adhesion and viability on other surfaces, i.e., directly on glass, were assessed for PEMs on glass and on cell culture flask polystyrene (FIG. 17). A live/dead assay revealed about 99% of living cells after 24 h. The cells showed similar behavior when seeded on the other surfaces to cells on the PET membrane, i.e., the different surfaces have no influence on cell adhesion and viability. Specifically, FIG. 17 shows cell adhesion and viability on standard cell culture surfaces. The behavior of NIH-3T3 cells did not significantly differ on the various surfaces. After 24 hours approximately 99% of the cells were alive. The scale bars in the squares are each 50 μm.

Many other benefits will no doubt become apparent from future application and development of this technology.

All patents, applications, and articles noted herein are hereby incorporated by reference in their entirety.

As described hereinabove, the present subject matter overcomes many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A layered assembly for use in dielectrophoresis (DEP), the assembly comprising:
   a polyester permeable membrane defining an outer face;
   at least one electrically conductive member disposed on the outer face of the membrane; and
   a layered composition disposed on at least one of the outer face of the membrane and the at least one electrically conductive member, the layered composition including (i) at least one layer of an adhesion material, and (ii) a layer of a polycation material disposed on the at least one layer of the adhesion material.

2. The layered assembly of claim 1 wherein the polyester membrane includes polyethylene terephthalate (PET).

3. The layered assembly of claim 1 wherein the polycation material is poly(allylamine hydrochloride) (PAH).

4. The layered assembly of claim 1 wherein the adhesion material is fibronectin (FN).

5. A method for retaining cells and bioparticles along a target surface during dielectrophoresis (DEP), the method comprising:
   providing a system for performing dielectrophoresis including provisions for generating a non-uniform electric field proximate to the target surface;
   wherein the target surface comprises a polyester permeable membrane defining an outer face;
   at least one electrically conductive member disposed on the outer face of the membrane; and
   applying a layered composition on the target surface, the layered composition including (i) at least one layer of an adhesion material, and (ii) a layer of a polycation material disposed on the at least one layer of the adhesion material, the layer of the polycation material providing an exposed face for retaining cells and bioparticles;
   performing dielectrophoresis such that cells and bioparticles contact the exposed face of the layered composition on the target surface, whereby the cells and bioparticles are retained on the exposed face of the layered composition at the target surface.

6. The method of claim 5 wherein the bioparticles include living cells.

7. The method of claim 6 wherein applying the layered composition includes an operation of depositing a first layer of the adhesion material on the target surface and then adsorbing a second layer of the polycation material on the deposited first layer of the adhesion material.

8. The method of claim 5 wherein the target surface includes a plurality of electrically conductive members disposed on a polyester permeable membrane.

9. The method of claim 5 wherein the polycation material is poly(allylamine hydrochloride) (PAH).

10. The method of claim 5 wherein the adhesion material is fibronectin (FN).

* * * * *